(12) United States Patent
Al-Jilaihawi

(10) Patent No.: US 10,507,301 B2
(45) Date of Patent: Dec. 17, 2019

(54) PIGTAIL FOR OPTIMAL AORTIC VALVULAR COMPLEX IMAGING AND ALIGNMENT

(71) Applicant: Cedars-Sinai Medical Center, Los Angeles, CA (US)

(72) Inventor: Hasanian Al-Jilaihawi, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 15/103,690

(22) PCT Filed: Jan. 30, 2015

(86) PCT No.: PCT/US2015/013956
§ 371 (c)(1),
(2) Date: Jun. 10, 2016

(87) PCT Pub. No.: WO2015/117025
PCT Pub. Date: Aug. 6, 2015

(65) Prior Publication Data
US 2016/0310699 A1   Oct. 27, 2016

Related U.S. Application Data

(60) Provisional application No. 61/934,250, filed on Jan. 31, 2014.

(51) Int. Cl.
*A61M 25/00* (2006.01)
*A61B 6/00* (2006.01)
(Continued)

(52) U.S. Cl.
CPC ......... *A61M 25/0071* (2013.01); *A61B 5/055* (2013.01); *A61B 5/6857* (2013.01);
(Continued)

(58) Field of Classification Search
CPC ......... A61B 5/00; A61B 8/00; A61M 25/0071
See application file for complete search history.

(56) References Cited

U.S. PATENT DOCUMENTS

| 4,694,838 | A | * | 9/1987 | Wijayarthna | ......... | A61M 5/007 600/435 |
| 4,738,667 | A | * | 4/1988 | Galloway | ............. | A61M 25/04 604/530 |

(Continued)

FOREIGN PATENT DOCUMENTS

| CN | 101489504 A | 7/2009 |
| CN | 104220028 A | 12/2014 |

(Continued)

OTHER PUBLICATIONS

PCT/US2014/069849 International Preliminary Report on Patentability dated Jun. 14, 2016; 7 pages.

(Continued)

*Primary Examiner* — Luther Behringer
*Assistant Examiner* — Sean D Mattson
(74) *Attorney, Agent, or Firm* — Nixon Peabody LLP

(57) ABSTRACT

Devices, systems and methods using two, three or more pigtails for precisely imaging an aortic valve complex with minimal contrast and/or for advancing an instrument, such as a wire, or device, such as a transcatheter valve, across an aortic valve. These devices, systems and methods may be used to diagnose and/or treat patients with aortic stenosis, other valvular heart disease or other cardiovascular or non cardiovascular disease, facilitating precise contrast or drug or device delivery, precise pressure measurement and/or precise drainage or sampling.

22 Claims, 12 Drawing Sheets

(51) Int. Cl.
*A61F 2/24* (2006.01)
*A61M 31/00* (2006.01)
*A61B 6/03* (2006.01)
*A61B 8/08* (2006.01)
*A61B 5/055* (2006.01)
*A61B 5/00* (2006.01)
*A61M 5/00* (2006.01)
*A61M 25/01* (2006.01)
*A61M 25/06* (2006.01)
*A61B 8/12* (2006.01)

(52) U.S. Cl.
CPC .............. *A61B 6/032* (2013.01); *A61B 6/503* (2013.01); *A61B 8/0883* (2013.01); *A61B 8/481* (2013.01); *A61F 2/2427* (2013.01); *A61M 5/007* (2013.01); *A61M 25/007* (2013.01); *A61M 25/0108* (2013.01); *A61M 31/005* (2013.01); *A61B 6/481* (2013.01); *A61B 8/085* (2013.01); *A61B 8/12* (2013.01); *A61M 2025/0681* (2013.01)

(56) References Cited

U.S. PATENT DOCUMENTS

| | | |
|---|---|---|
| 5,423,829 A | 6/1995 | Pham et al. |
| 5,964,744 A * | 10/1999 | Balbierz ............. A61L 27/34 |
| | | 604/530 |
| 5,964,797 A | 10/1999 | Ho |
| 5,972,019 A | 10/1999 | Engleson et al. |
| 6,059,779 A | 5/2000 | Mills |
| 6,086,557 A * | 7/2000 | Morejohn ......... A61M 25/0041 |
| | | 604/101.01 |
| 6,217,611 B1 | 4/2001 | Klostermeyer |
| 6,287,277 B1 | 9/2001 | Yan |
| 6,350,282 B1 | 2/2002 | Eberhardt |
| 6,589,230 B2 | 7/2003 | Gia et al. |
| 6,953,473 B2 | 10/2005 | Porter |
| 6,964,657 B2 | 11/2005 | Cragg et al. |
| 6,976,965 B2 | 12/2005 | Corl et al. |
| 7,134,994 B2 | 11/2006 | Alpert et al. |
| 7,340,288 B1 | 3/2008 | Karicherla et al. |
| 7,935,144 B2 | 5/2011 | Robin et al. |
| 8,070,800 B2 | 12/2011 | Lock et al. |
| 8,092,524 B2 | 1/2012 | Nugent et al. |
| 8,372,069 B2 | 2/2013 | Kassab |
| 8,377,112 B2 | 2/2013 | Griffin et al. |
| 8,408,214 B2 | 4/2013 | Spenser |
| 8,430,927 B2 | 4/2013 | Bonhoeffer |
| 8,491,648 B2 | 7/2013 | Hassan et al. |
| 2002/0169474 A1 | 11/2002 | Kusleika et al. |
| 2004/0172081 A1 | 9/2004 | Wang |
| 2005/0203425 A1 | 9/2005 | Langston |
| 2005/0240200 A1 | 10/2005 | Bergheim |
| 2005/0256566 A1 | 11/2005 | Gabbay |
| 2005/0267010 A1 | 12/2005 | Goodson et al. |
| 2006/0064114 A1 | 3/2006 | Obitsu et al. |
| 2006/0015530 A1 | 7/2006 | Freudenthal |
| 2006/0155305 A1 | 7/2006 | Freudenthal |
| 2006/0287719 A1 | 12/2006 | Rowe et al. |
| 2007/0050021 A1 | 3/2007 | Johnson |
| 2007/0203562 A1 | 8/2007 | Malewicz et al. |
| 2008/0027334 A1 | 1/2008 | Langston |
| 2008/0033467 A1 | 2/2008 | Miyamoto et al. |
| 2008/0183273 A1 | 7/2008 | Mesana et al. |
| 2008/0221551 A1 | 9/2008 | Goodson et al. |
| 2008/0306499 A1 | 12/2008 | Katoh et al. |
| 2008/0319541 A1 | 12/2008 | Filsoufi |
| 2009/0082678 A1 | 3/2009 | Smith |
| 2009/0248143 A1 | 10/2009 | Laham |
| 2009/0259292 A1 | 10/2009 | Bonhoeffer |
| 2009/0276040 A1 | 11/2009 | Rowe et al. |
| 2010/0030330 A1 | 2/2010 | Bobo et al. |
| 2010/0094209 A1* | 4/2010 | Drasler ............. A61M 25/1002 |
| | | 604/95.04 |
| 2010/0168840 A1 | 7/2010 | Kassab |
| 2010/0185275 A1 | 7/2010 | Richter et al. |
| 2010/0191272 A1 | 7/2010 | Keating |
| 2010/0211094 A1 | 8/2010 | Sargent |
| 2010/0331948 A1 | 12/2010 | Turovskiy et al. |
| 2011/0137397 A1 | 6/2011 | Chau et al. |
| 2012/0059458 A1 | 3/2012 | Buchbinder et al. |
| 2012/0130230 A1 | 5/2012 | Eichler et al. |
| 2012/0158129 A1 | 6/2012 | Duffy et al. |
| 2012/0283757 A1 | 11/2012 | Miller et al. |
| 2012/0283812 A1 | 11/2012 | Lagodzki et al. |
| 2012/0283820 A1 | 11/2012 | Tseng et al. |
| 2012/0310328 A1 | 12/2012 | Olson et al. |
| 2013/0090726 A1 | 4/2013 | Rowe et al. |
| 2013/0109960 A1* | 5/2013 | Stinis ............... A61M 25/0041 |
| | | 600/424 |
| 2013/0116779 A1 | 5/2013 | Weber |
| 2013/0166017 A1 | 6/2013 | Cartledge et al. |
| 2013/0190857 A1 | 7/2013 | Mitra et al. |
| 2013/0190865 A1 | 7/2013 | Anderson |
| 2013/0261738 A1 | 10/2013 | Clague et al. |
| 2013/0261739 A1 | 10/2013 | Kuehn |
| 2013/0274618 A1 | 10/2013 | Hou et al. |
| 2013/0331864 A1 | 12/2013 | Jelich et al. |
| 2013/0331921 A1 | 12/2013 | Roubin |
| 2014/0114402 A1 | 4/2014 | Ahlberg et al. |
| 2014/0135799 A1 | 5/2014 | Henderson |
| 2014/0171958 A1 | 6/2014 | Baig |
| 2014/0194981 A1 | 7/2014 | Menk et al. |
| 2014/0200662 A1 | 7/2014 | Eftel et al. |
| 2014/0222144 A1 | 8/2014 | Eberhardt et al. |
| 2014/0236287 A1 | 8/2014 | Clague et al. |
| 2014/0243966 A1 | 8/2014 | Garde et al. |
| 2014/0277419 A1 | 9/2014 | Garde et al. |
| 2014/0303719 A1 | 10/2014 | Cox et al. |
| 2014/0350669 A1 | 11/2014 | Gillespie et al. |
| 2016/0206424 A1 | 7/2016 | Al-Jilaihawi et al. |
| 2016/0228013 A1 | 8/2016 | Al-Jilaihawi et al. |
| 2016/0228241 A1 | 8/2016 | Al-Jilaihawi et al. |
| 2016/0235422 A1 | 8/2016 | Al-Jilaihawi et al. |
| 2016/0302920 A1 | 10/2016 | Al-Jilaihawi |
| 2018/0078363 A1 | 3/2018 | Al-Jilaihawi |

FOREIGN PATENT DOCUMENTS

| | | |
|---|---|---|
| CN | 104334119 A | 2/2015 |
| CN | 105611871 A | 5/2016 |
| CN | 105611889 A | 5/2016 |
| CN | 105744969 A | 7/2016 |
| CN | 105764447 A | 7/2016 |
| EP | 2732796 A1 | 5/2014 |
| EP | 3054838 A1 | 8/2016 |
| EP | 3057522 A1 | 8/2016 |
| EP | 3079633 A1 | 10/2016 |
| EP | 3099345 A1 | 12/2016 |
| WO | 1996017644 | 6/1996 |
| WO | 1998048879 | 11/1998 |
| WO | 99/15223 A1 | 4/1999 |
| WO | 99/15227 A1 | 4/1999 |
| WO | 1999015223 | 4/1999 |
| WO | 0249511 | 6/2002 |
| WO | 2005059379 A1 | 6/2005 |
| WO | 2007081820 A1 | 7/2007 |
| WO | 2010085659 A1 | 7/2010 |
| WO | 2011039091 A1 | 4/2011 |
| WO | 2012009675 A2 | 1/2012 |
| WO | 2012161769 A1 | 11/2012 |
| WO | 2012/173697 A1 | 12/2012 |
| WO | 2013061231 A1 | 5/2013 |
| WO | 2014145469 A1 | 9/2014 |
| WO | 2015/054296 A1 | 4/2015 |
| WO | 2015/057735 A1 | 4/2015 |
| WO | 2015/057995 A2 | 4/2015 |
| WO | 2015/058001 A1 | 4/2015 |
| WO | 2015/089334 A1 | 6/2015 |

(56) References Cited

FOREIGN PATENT DOCUMENTS

| WO | 2015/117025 A1 | 8/2015 |
|----|---------------|--------|
| WO | 2016145250 A1 | 9/2016 |

OTHER PUBLICATIONS

PCT/US2015/013956 International Preliminary Report on Patentability dated Aug. 2, 2016; 7 pages.
PCT/US2014/059547 International Preliminary Report on Patentability dated Apr. 12, 2016; 6 pages.
PCT/US2014/060526 International Search Report and Written Opinion dated Feb. 10, 2015; 7 pages.
PCT/US2014/060957 International Search Report and Written Opinion dated Apr. 1, 2015; 10 pages.
PCT/US2014/060966 International Search Report and Written Opinion dated Jan. 29, 2015; 6 pages.
PCT/US2014/059547 International Search Report and Written Opinion dated Mar. 3, 2015; 9 pages.
PCT/US2014/069849 International Search Report and Written Opinion dated Mar. 2, 2015; 8 pages.
PCT/US2015/013956 International Search Report and Written Opinion dated Jun. 26, 2015; 10 pages.
Astarci et al. Transapical explantation of an embolized transcatheter valve. Interact Cardiovasc Thorac Surg (2011). 13:1-2.
Blows et al. The pressure wire in practice. Heart (2007). 93:419-422.
Bonhoeffer et al. The multi-track angiography catheter: a new tool for complex catheterisation in congenital heart disease. Heart (1996). 76:173-177.
Chiam et al. Percutaneous Transcatheter Mitral Valve Repair. J Am Coll Cardiol (2011). 4(1):1-13.
Ho, S.Y. Structure and anatomy of the aortic root. Eur J Echocardiogr (2009). 10:i3-i10.
Jolicoeur et al. Tiara: A Novel Catheter-Based Mitral Valve Bioprosthesis Initial Experiments and Short-Term Pre-Clinical Results. J Am Coll Cardiol (2012). 60(15)1430-1431.
Lange et al. Diagnostic Cardiac Catheterization. Circulation (2003). 107:e111-e113.
Masson et al. Percutaneous Treatment of Mitral Regurgitation. Circ Cardiovasc Interv (2009). 2:140-146.
McCarthy et al. Anatomy of the mitral valve: understanding the mitral valve complex in mitral regurgitation. Eur J Echocardiogr (2010). 11:i3-i9.
Ormiston et al. Bioabsorbable Coronary Stents (2009). Circ Cardiovasc Interv (2009). 2:255-260.
Sievers et al. The everyday used nomenclature of the aortic root components: the tower of Babel? Eur J Cardio-Thorac Surg (2011). 0:1-5.
Sinning et al. Aortic Regurgitation Index Defines Severity of Pen-Prosthetic Regurgitation and Predicts Outcome in Patients After Transcatheter Aortic Valve Implantation. J Am Coll Cardiol (2012). 59(13):1134-1141.
Tonino et al. Fractional Flow Reserve versus Angiography for Guiding Percutaneous Coronary Intervention. New Engl J Med (2009). 360(3):213-224.
Tsai et al. Transcatheter Retrieval of Dislodged Port-A Catheter Fragments: Experience with 47 Cases. Acta Cardiol Sin (2006). 22:221-228.
Van Mieghem et al. Anatomy of the Mitral Valvular Complex and Its Implications for Transcatheter Interventions for Mitral Regurgitation. J Am Coll Cardiol (2010). 56(8):617-626.
PCT/US2014/060526 International Preliminary Report on Patentability dated Apr. 19, 2016, 7 pages.
PCT/US2014/060957 International Preliminary Report on Patentability dated Apr. 19, 2016, 10 pages.
PCT/US2014/060966 International Preliminary Report on Patentability dated Apr. 19, 2016, 6 pages.
Extended European Search Report for EP Application No. 14853895.2 dated May 10, 2017, 8 pages.
Partial Supplementary European Search Report for EP Application No. 14851950.7 dated Apr. 10, 2017, 6 pages.
Extended European Search Report for EP Application No. 14869869.9 dated May 4, 2017, 7 pages.
PCT/US2016/021866 International Search Report and Written Opinion dated May 23, 2016, 11 pages.
EESR for PCT/US2015/013956 dated Sep. 5, 2017, 8 pages.
PCT/US2016/021866 International Preliminary Report on Patentability dated Sep. 21, 2017, 9 pages.
EP16762555.7 Supplementary European Search Report dated Oct. 5, 2018, 8 pages.

\* cited by examiner

PIGTAIL FOR OPTIMAL AORTIC VALVULAR COMPLEX IMAGING AND ALIGNMENT

CROSS-REFERENCE TO RELATED APPLICATIONS

This application is a National Phase of International Application No. PCT/US2015/013956 filed Jan. 30, 2015, currently pending, which designated the U.S. and that International Application was published under PCT Article 21(2) in English, which also includes a claim of priority under 35 U.S.C. § 119(e) to U.S. provisional patent application No. 61/934,250 filed Jan. 31, 2014, the entirety of which is hereby incorporated by reference.

FIELD OF INVENTION

This invention relates to devices, systems and methods for aortic valve complex imaging and/or for transcatheter aortic valve replacement, which may be used to diagnose and/or treat aortic valve diseases.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Prior Transcatheter Valve Therapies

Valvular heart disease is characterized by damage to or a defect in one of the four heart valves: the mitral, aortic, tricuspid or pulmonary. The mitral and tricuspid valves control the flow of blood between the atria and the ventricles (the upper and lower chambers of the heart). The pulmonary valve controls the blood flow from the heart to the lungs, and the aortic valve governs blood flow between the heart and the aorta, and thereby to the blood vessels in the rest of the body. The mitral and aortic valves are the ones most frequently affected by valvular heart disease. Transcatheter valve therapies are one treatment option for patients. For example, transcatheter aortic valve replacement (TAVR, also known as TAVI or transcatheter aortic valve implantation) is a procedure for select patients with severe symptomatic aortic stenosis (narrowing of the aortic valve opening) who are not candidates for traditional open chest surgery or are high-risk operable candidates. A replacement valve is inserted percutaneously using a catheter and implanted in the orifice of the native aortic valve. Replacement valves may be artificial (prosthetic valves) or made from animal tissue (bioprosthetic valves). The type of replacement valve selected depends on the patient's age, condition, and the specific valve affected.

Optimal orientation of X-ray fluoroscopic imaging is fundamental to the success of TAVR. An aortic valve has three leaflets: the right coronary leaflet, the left coronary leaflet, and the non-coronary leaflet. During a TAVR procedure, a conventional pigtail catheter is normally oriented in the non-coronary leaflet and used to inject a contrast dye for X-ray imaging. Since dye injection through the pigtail catheter takes place only in the non-coronary leaflet, the other two leaflets depend on dye spilling back and over to be imaged. Hence, this imaging method is unreliable, and may require multiple injections and large amount of contrast dye for completely visualizing the aortic root and determining the co-axial plane of radiographic projection. This imaging method is sometimes supplemented with pre-procedural imaging such as CT scanning Reducing the amount of contrast dye used is of particular benefit to patients on certain drugs or with one or more pre-existing medical condition, such as diabetes, heart failure or reduced kidney function. Such patients are at a greater risk of prolonged or permanent damage from the dye, often resulting in the need for further medical attention or dialysis. A focused and more precise delivery of contrast may also limit the patient's exposure to radiation.

Another challenging step during a TAVR procedure is to advance an instrument (e.g., a guidewire, a catheter, and/or a pressure sensor) across the aortic valve retrogradely from the aorta to the left ventricle. This step of retrograde crossing is usually performed with a curved catheter (for example, an AL1, AL2 or JR4 catheter) and a straight wire, and sometimes requires considerable manipulation, especially for an aortic valve with a high level of stenosis. Accordingly, a need exists for an improved system for efficiently orienting a catheter system with respect to internal vessel and cardiac structures and additionally for imaging internal vessel and valve structures, for example, the aortic valve.

SUMMARY OF THE INVENTION

The following embodiments and aspects thereof are described and illustrated in conjunction with compositions, devices, systems and methods which are meant to be exemplary and illustrative, not limiting in scope.

Overview of Invention

In order to solve the problems discussed above, the applicants have developed a system of catheters incorporating two, three, or more distal branches that can properly align and orient a catheter system for either: (1) injecting a contrast dye, (2) imaging an aortic valve complex or other internal structure (e.g, various blood vessels), and/or (3) for advancing an instrument across an aortic valve or other valvular structures. For example, the distal branches may form three pigtails that can each engage the base of each of the three leaflets of an aortic valve. By lining up and engaging each of the three pigtails, clear visualization of a co-axial radiographic projection can be obtained, even without injection of a contrast dye, in order to efficiently orient the device for transcatheter aortic valve therapies. The device also has a central lumen that, when positioned with the three distal branches as described herein, is oriented co-axially with the orifice of the aortic valve complex. Accordingly, once the central lumen and valve orifice are lined up, another instrument such as a wire can be passed centrally via the central lumen to cross the aortic valve orifice retrogradely in a more efficient manner. In some embodiments, each of the multiple pigtails of the device may be advanced independently of one another to optimize position. In some embodiments, each of the multiple pigtails can be advanced independently, with or without a guiding wire, to different vessels, chambers, or cavities within or outside the heart or vascular system, to facilitate focused contrast delivery or drug delivery or sampling of blood or fluid through their respective central lumens or pressure comparison via their respective central lumens. In some embodiments, the multiple pigtail device may be of larger profile and may be used as a delivery sheath designed to facilitate precise device orientation through its orientation with native anatomy, for example, but not restricted to, delivery of a transcatheter aortic valve.

Embodiments of Invention

In various embodiments, provided herein is a device for imaging an aortic valve complex and/or for advancing an instrument across an aortic valve retrogradely. The device may include: a catheter comprising an interior wall and an exterior wall, wherein the catheter has a proximal portion, a distal portion, and a center portion between the proximal portion and the distal portion. The interior wall forms a central lumen along the longitudinal axis of the catheter. The interior wall and the exterior wall form a peripheral lumen around the central lumen along the longitudinal axis of the catheter. The interior wall and the exterior wall form three distal branches at the distal portion of the catheter, and the peripheral lumen branches into three peripheral lumen branches inside the three distal branches. In accordance with the present invention, each of the three distal branches can comprises one radiographic marker and/or one or more side openings at or near the distal end of the distal branch. In accordance with the present invention, the device further comprises a tube, wherein the tube is inserted into the central lumen and may be advanced over a guide wire to cross a valve or stenosis independent from the other components of the device.

In various embodiments, provided herein is a device for imaging an aortic valve complex. Various embodiments of the present invention provide a device for imaging an aortic valve complex. The device may include a catheter comprising a wall, wherein the catheter has a proximal portion, a distal portion, and a center portion between the proximal portion and the distal portion. The wall forms one tube along the longitudinal axis of the catheter at the center portion and forms two, three, four or more distal branches at the distal portion. Accordingly, the lumen of the tube branches into two, three, four or more lumen branches inside the two, three, four or more distal branches. In accordance with the present invention, each distal branch can comprises one radiographic marker and/or one or more side openings at or near the distal end of the distal branch.

In various embodiments, provided herein is a method for imaging an aortic valve complex. The method may include the following steps: (1) providing an outer sheath; (2) maneuvering the outer sheath to reach the sinotubular junction of a subject; (3) providing a device comprising: a catheter comprising an interior wall and an exterior wall, wherein the catheter has a proximal portion, a distal portion, and a center portion between the proximal portion and the distal portion, wherein the interior wall forms a central lumen along the longitudinal axis of the catheter, wherein the interior wall and the exterior wall form a peripheral lumen around the central lumen along the longitudinal axis of the catheter, wherein the interior wall and the exterior wall form three distal branches at the distal portion of the catheter, wherein the peripheral lumen branches into three peripheral lumen branches inside the three distal branches, and wherein each of the three distal branches comprises one or more side openings at or near the distal end of the distal branch; (4) inserting the device into the outer sheath, wherein the three distal branches are straightened inside the outer sheath; (5) advancing the device of out of the outer sheath, wherein the three distal branches are pigtail-shaped or J-shaped outside the outer sheath; (6) engaging each of the three aortic leaflets of the subject with one distal branch; (7) injecting a contrast dye to the aortic valve complex of the subject through the peripheral lumen; and (8) imaging the aortic valve complex of the subject.

In various embodiments, provided herein is a method for imaging an aortic valve complex. The method may include the following steps: (1) providing an outer sheath; (2) maneuvering the outer sheath to reach the sinotubular junction of a subject; (3) providing a device comprising: a catheter comprising an interior wall and an exterior wall, wherein the catheter has a proximal portion, a distal portion, and a center portion between the proximal portion and the distal portion, wherein the interior wall forms a central lumen along the longitudinal axis of the catheter, wherein the interior wall and the exterior wall form a peripheral lumen around the central lumen along the longitudinal axis of the catheter, wherein the interior wall and the exterior wall form three distal branches at the distal portion of the catheter, wherein the peripheral lumen branches into three peripheral lumen branches inside the three distal branches, and wherein each of the three distal branches comprises one radiographic marker at or near the distal end of the distal branch; (4) inserting the device into the outer sheath, wherein the three distal branches are straightened inside the outer sheath; (5) advancing the device out of the outer sheath, wherein the three distal branches are pigtail-shaped or J-shaped outside the outer sheath; (6) engaging each of the three aortic leaflets of the subject with one distal branch; and (7) imaging the aortic valve complex of the subject and the radiographic markers.

In various embodiments, provided herein is a method for imaging an aortic valve complex. The method may include the following steps: (1) providing an outer sheath; (2) maneuvering the outer sheath to reach the sinotubular junction or the aortic root just above the aortic valve of a subject; (3) providing a device comprising: a catheter comprising an interior wall and an exterior wall, wherein the catheter has a proximal portion, a distal portion, and a center portion between the proximal portion and the distal portion, wherein the interior wall forms a central lumen along the longitudinal axis of the catheter, wherein the interior wall and the exterior wall form a peripheral lumen around the central lumen along the longitudinal axis of the catheter, wherein the interior wall and the exterior wall form three distal branches at the distal portion of the catheter, wherein the peripheral lumen branches into three peripheral lumen branches inside the three distal branches, and wherein each of the three distal branches comprises one radiographic marker and one or more side openings at or near the distal end of the distal branch; (4) inserting the device into the outer sheath, wherein the three distal branches are straightened inside the outer sheath; (5) advancing the device out of the outer sheath, wherein the three distal branches are pigtail-shaped or J-shaped outside the outer sheath; (6) engaging each of the three aortic leaflets of the subject with one distal branch; and (7) imaging the aortic valve complex of the subject and the radiographic markers. In various embodiments, the method further comprises, prior to step (7), injecting a contrast dye to the aortic valve complex of the subject through the peripheral lumen.

In various embodiments, provided herein is a method for imaging an aortic valve complex. The method may include the following steps: (1) providing an outer sheath; (2) maneuvering the outer sheath to reach the sinotubular junction or aortic root, just above the aortic valve, of a subject; (3) providing a device, comprising: a catheter comprising a wall, wherein the catheter has a proximal portion, a distal portion, and a center portion between the proximal portion and the distal portion, wherein the wall forms one tube along the longitudinal axis of the catheter at the center portion and forms two, three, four or more distal branches at the distal portion, wherein the lumen of the tube branches into two, three, four or more lumen branches inside the two, three, four or more distal branches; (4) inserting the device into the outer sheath, wherein the two, three, four or more distal branches are straightened inside the outer sheath; (5) advancing the device out of the outer sheath, wherein the two, three, four or more distal branches are pigtail-shaped or J-shaped outside the outer sheath; (6) engaging each aortic leaflet of the subject with one distal branch; (7) injecting a contrast dye to the aortic valve complex of the subject through the catheter; and (8) imaging the aortic valve complex of the subject.

In an embodiment, the central lumen of the catheter is relatively large (for example, 8-24 Fr) and acts as a long delivery sheath for a balloon aortic valvuloplasty (BAV) balloon or TAVR delivery system. In a further embodiment, the device comprises a mechanism (for example, a radiographic maker) for aligning the ridges, lines, points or alternative markers of the central lumen and the BAV or TAVR delivery system to facilitate precise rotational positioning of the BAV or TAVR delivery system in relation to the three native aortic valve leaflets.

In another embodiment, in a patient with anatomical variation where the native aortic valve is bicuspid rather than tricuspid, a device having two rather than three distal branches is employed in correspondence to the two-leaflet configuration of the native aortic valve with anatomical variation. In a further embodiment, the device may be used for the imaging and correct orientation of other valves. In accordance with the invention, the number of distal branches corresponds to the number of leaflets in a native valve of interest. For instance, when the valve of interest is the mitral valve, which has two leaflets, a device having correspondingly two distal branches would be employed.

Further Applications of Invention

In various embodiments, the device may be used to facilitate treatment of any vessel stenosis that requires a balloon or stent therapy, any aneurysmal vessel that requires a stent therapy, any vascular sac that requires a vascular closure, including but not limited to the left atrial appendage. In some embodiments, each of the pigtails of the device may be advanced independently of one another to optimize position. In some embodiments, each of the multiple pigtails can be advanced independently, with or without a guiding wire, to different vessels to facilitate focused contrast delivery through their respective central lumens or pressure comparison via their respective central lumens. In various embodiments, the distal branches of the device may be used at both cardiac and extracardiac sites to administer medications, inject contrast dye into a cavity, vessel or structure, drain or sample blood or fluid or irrigate. Examples of extracardiac applications include, but are not limited to, drainage of fluid from the peritoneal space with ascites, injecting contrast dye into the abdominal cavity, or transurethral irrigation of the bladder in the setting of hematuria.

In another embodiment, the central shaft formed by the interior lumen of the catheter, may be advanced over a wire independently of the other layers of the catheter to cross a valve or stenosis.

In another embodiment, the double/triple pigtail device has no central lumen and is simply two/three or more hollow tubes connected to a common hollow tube from which they branch and is inserted through the outer sheath to the appropriate position. In various embodiments, the device may not have continuous lumens and may be only used for imaging without contrast dye.

BRIEF DESCRIPTION OF FIGURES

Exemplary embodiments are illustrated in the referenced figures. It is intended that the embodiments and figures disclosed herein are to be considered illustrative rather than restrictive.

FIG. 2A depicts a cross sectional view of a patient's heart with an outer sheath 102 being advanced towards the aortic valve. FIG. 2B depicts a cross-sectional view of a patient's heart with a catheter 101 being advanced distally to the tip of the outer sheath 102. FIG. 2C depicts a cross-sectional view of a patient's heart and the catheter 101 being extended from the outer sheath 102 and the distal branches extending out towards the aortic valve leaflets. FIG. 2D depicts a cross sectional view of a patient's heart and the distal branches of the catheter 101 including side openings 108 on the distal branches. FIG. 2E depicts a cross sectional view of a patient's heart a catheter 101, and a guidewire 201.

FIG. 3A depicts a cross sectional view of a patient's heart with an outer sheath 102 being advanced towards the aortic valve. FIG. 3B depicts a cross-sectional view of a patient's heart with a catheter 101 being advanced distally to the tip of the outer sheath 102. FIG. 3C depicts a cross-sectional view of a patient's heart and the catheter 101 being extended from the outer sheath 102 and the distal branches extending out towards the aortic valve leaflets. FIG. 3D depicts a cross sectional view of a patient's heart and the distal branches of the catheter 101 including radiographic markers 109 on the distal branches.

FIG. 4A depicts a cross section of a distal branch with side openings 108. FIG. 4B depicts a cross section of a distal branch with a radiographic marker 109. FIG. 4C depicts a cross section of a distal branch with a radiographic marker 109 and a side opening 108.

DETAILED DESCRIPTION OF THE INVENTION

Figure 1:
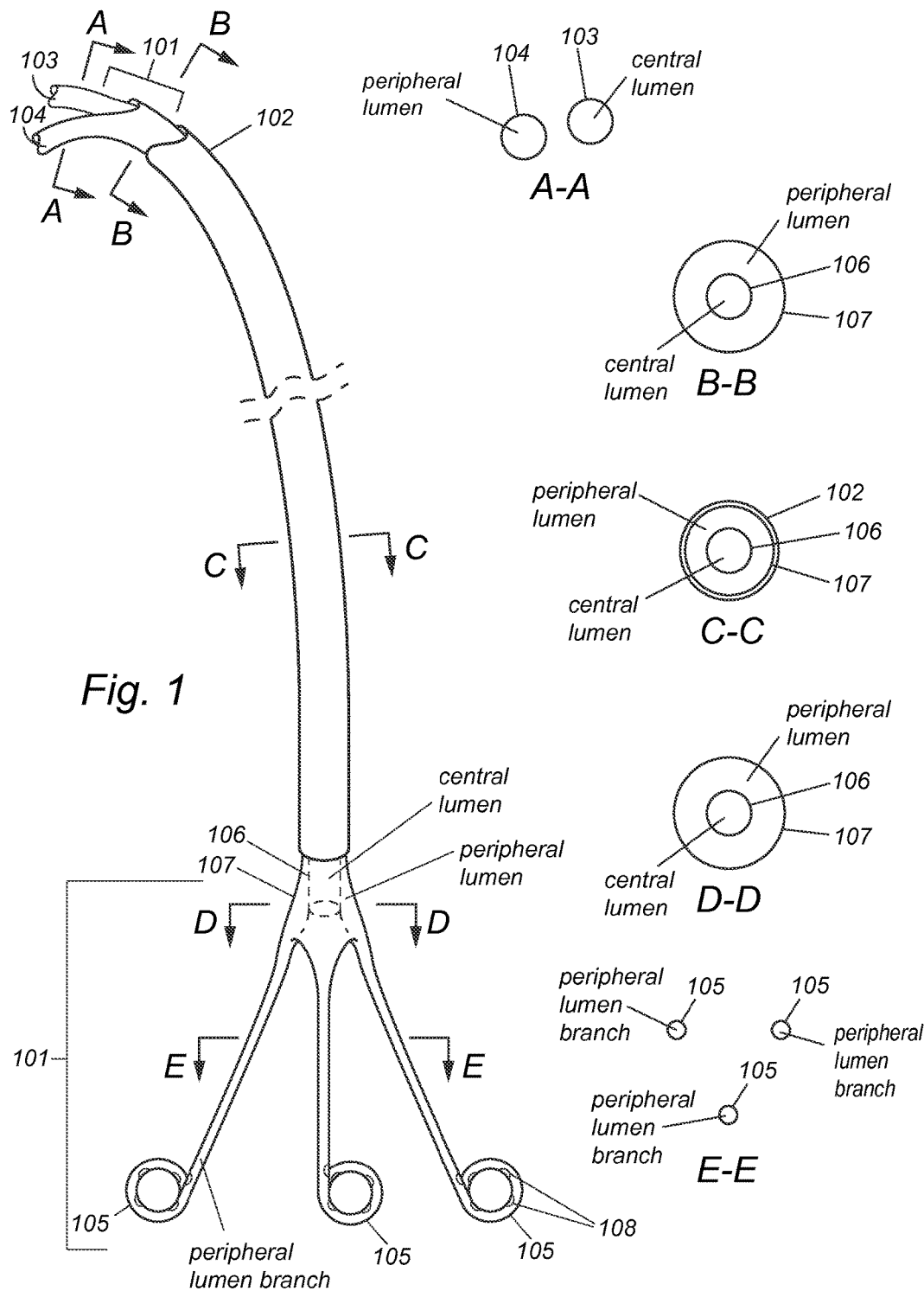
FIG. 1 depicts a cross sectional view of an embodiment of a catheter (101), an outer sheath covering the catheter (102), a central lumen inlet (103), a peripheral lumen inlet (104), three distal branches of the catheter (105), an interior wall of the catheter (106), and an exterior wall of the catheter (107). Panel A-A is a cross-section view of the device at its proximal end. Panel B-B is a cross-section view of the proximal portion of the device. Panel C-C is a cross-section view of the center portion of the device. Panel D-D is a cross-section view of the distal portion of the device. Panel E-E is a cross-section view of the three distal branches 105 on the distal portion of the device.

The applicants have developed a system of catheters incorporating two, three, or more distal branches that can properly align and orient a catheter system for either: (1) injecting a contrast dye or drug, (2) draining or sampling blood or fluid, (3) imaging an aortic valve complex or other internal structures (e.g. vessels), (4) calculating pressure differences between the branches or cavities, (5) for advancing an instrument across an aortic valve, other valve, or other internal structures. For example, the three distal branches may form or end in three pigtails that can each be navigated to the one of the three aortic valve leaflets in order to engage the base of each of the three leaflets. By lining up the three distal branches with the base of the leaflets, the device will be efficiently oriented to (1) inject contrast dye to visualize the leaflets and/or (2) visualize the valvular complex using radiographic markers inside the distal branches, The device may also have a central lumen that is oriented co-axially with the orifice of the aortic valve complex, when the distal branches are appropriately positioned by engaging or contacting the base of the leaflets of a valve complex. Accordingly, once the central lumen and valve orifice are lined up, another instrument such as a wire can be passed centrally via the central lumen to cross the aortic valve orifice retrogradely in a more efficient manner.

In some embodiments, each of the multiple pigtails of the device may be advanced independently of one another to optimize position. This may allow a caregiver to optimally position each of the branches independently, in order to allow the device to accommodate a wider range of variability in physiology and different types of physiological structures. In these embodiments, the lumens and sidewall of the distal branches may slide with respect to the central lumen. In some embodiments, this will allow the distal branches to telescope from the central lumen and rotate to optimally orient the device. In some embodiments, each of the multiple pigtails can be advanced independently, with or without a guiding wire, to different vessels, chambers, or cavities within or outside the heart or vascular system, to facilitate focused contrast delivery or drug delivery through their respective central lumens or pressure comparison via their respective central lumens. In some embodiments, the multiple pigtail device may be of larger profile and may be used as a delivery sheath designed to facilitate precise device orientation through its orientation with native anatomy, for example, but not restricted to, delivery of a transcatheter aortic valve.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

A non-limiting example of a device according to the present disclosure is shown in FIG. 1. The catheter 101 is covered by an outer sheath 102. The length of the catheter 101 may be but is not limited to about 90-300 cm depending on the precise application. The diameter of the catheter may be but is not limited to about 4-23 Fr. The length of the outer sheath 102 may be but is not limited to about 80-290 cm. The diameter of the outer sheath 102 may be but is not limited to about 5-24 Fr. The catheter 101 may have an interior wall 106 and an exterior wall 107. In some embodiments, a central lumen is defined by the interior wall 106 at the center of the catheter 101. The central lumen may be used for inserting another instrument (e.g., a guidewire, a catheter, and a pressure sensor). For example, the catheter 101 may be advanced over a guidewire in the central lumen to be guided to reach the sinotubular junction or other internal structure, or a guidewire may be inserted in the central lumen to be guided through an aortic valve orifice or other orifice that is co-axially aligned with the central lumen. Around the central lumen, a peripheral lumen may be formed between the interior wall 106 and the exterior wall 107. In other embodiments, the peripheral lumen may be formed by a separate tube and wall that may be able to move relative to the central lumen. This will allow the peripheral lumens (and therefore the distal branches 105) to be separately and independently extended and rotated with respect to the central lumen and each other. This may allow for optimal positioning of the distal branches 105. The peripheral lumen(s) may be used as a contrast dye reservoir for filling a contrast dye and/or as a fluid commutation channel for injecting a contrast dye or drug. For instance and as described below, the peripheral lumen may branch into two lumens, three lumens, four lumens, five lumens, six lumens, or other amount of lumens in the distal branches of the catheter 101 and allow the contrast dye to flow down the peripheral lumen into the distal branches 105 and out of the side openings of the distal branches. The diameter of the tubular interior wall may be but is not limited to about 1-6 Fr. The diameter of the tubular exterior wall may be but is not limited to about 2-8 Fr.

The catheter 101 has a proximal portion (close to a user, shown at the top), where the central lumen and the peripheral lumen each form two separate inlets 103 and 104. As described above, these may be formed by two separate, non-coaxial tubes, or coaxial tubes with an interior wall 106 and an exterior wall 107. The central lumen inlet 103 may be used for inserting another instrument (e.g., a guidewire, a catheter, and a pressure sensor). The peripheral lumen inlet 104 may be used for filling and/or injecting a contrast dye.

The catheter 101 may have a distal portion (away from a user, shown at the bottom), where, in some embodiments, the catheter 101 branches into two, three, four, five, six, or more distal branches 105 and the peripheral lumen accordingly branches into as many peripheral lumen branches inside the distal branches 105. The length of the distal branches 105 may be but is not limited to about 2-20 cm. The diameter of the distal branches 105 may be but is not limited to about 1-6 Fr.

In some embodiments, at or near the end of each distal branch 105, there are one or more side openings 108. Side openings 108 may be any suitable openings in the distal branches 105 of the catheter 108 that allow the contrast dye to flow out from the peripheral lumen into the heart. In some embodiments, side openings 108 may be a plethora of tiny openings to allow more even dispersal of the contrast dye into the cardiac space. In other embodiments, side openings may be one or two openings that are larger.

In some of the three branch embodiments, once the three distal branches 105 are extended from the sheath 102, the branches 105 spring out and extend to a natural orientation when they are not restrained by the sheath 102. The natural orientation positions the distal branches 105 so they are equally spaced from one another on a radial plane perpendicular to the longitudinal axis of the catheter. This spatial alignment is illustrated in panels E-E and D-D of FIGS. 1 and 5 respectively, where each of the lumen branches 105, and 505 are equally spaced from each other. When the distal portion is enclosed in the outer sheath 102, the three distal branches 105 are straightened.

In some embodiments, when the distal portion is exposed outside the outer sheath 102, the three distal branches 105 curl into a pigtail or J form. In other embodiments, the distal branches 105 may take on any other morphology that would prevent puncture of any cardiac structures and allow for positioning the three distal branches 105 in close proximity to the aortic valve leaflets. The three pigtails offer a unique advantage as they can deliver smaller amounts of contrast dye precisely to the base of each of the three cusps of an aortic valve, and the curved edge prevents the device from damaging the leaflets or other internal structures of the patient. Moreover, alignment of the three pigtails to approach the three leaflets can be used to determine the critical co-planar fluoroscopic projection, even without a contrast dye (for example, when the three pigtails are made of or impregnated with a radiographic material for clear visualization of the three pigtails themselves, or when radiographic markers are placed on the three pigtails for clear visualization of the tips of the three pigtails). The three pigtails also can orient the central lumen with respect to the orifice of the aortic valve so that another instrument such as a wire can be delivered retrogradely and precisely through the center of a stenotic valve, thereby increasing procedural efficiency. For example, if the distal branches are all aligned with the aortic valve leaflets, the central lumen will be aligned with the center of the aortic valve (in a cross section) which will be the most likely portion of the valve to have an opening.

Panels A-A through E-E show various cross-sections of various embodiments a device according to the present disclosure that illustrate the positioning of the various lumens. Panel A-A is a cross-section view of the device at its proximal end, showing the central lumen inlet 103 and the peripheral lumen inlet 104. Panel B-B is a cross-section view of the proximal portion of the device, showing the central lumen formed by the interior wall 106 and the peripheral lumen formed between the interior wall 106 and the exterior wall 107. Panel C-C is a cross-section view of the center portion of the device, showing the central lumen formed by the interior wall 106, the peripheral lumen formed between the interior wall 106 and the exterior wall 107, and the retractable outer sheath 102 covering the catheter 101. Panel D-D is a cross-section view of the distal portion of the device, showing the central lumen formed by the interior wall 106 and the peripheral lumen formed between the interior wall 106 and the exterior wall 107. Panel E-E is a cross-section view of the three distal branches 105 on the distal portion of the device. Various other orientations and morphologies of the valve could be utilized in order to provide a lumen for directing tools such as guidewires to the valve and another lumen for potentially injecting dye near the valve out of openings in the distal branches 105. For example, as described above, the central lumen may be formed by an interior wall 106, and the peripheral lumen may be formed from an exterior wall 107 that is not coaxial with the interior wall 106, and therefore forms two separate tubes. In some embodiments, the separate tubes may move in a longitudinal direction with respect to each other and rotate freely about a longitudinal axis.

Example 2

Figure 2A:
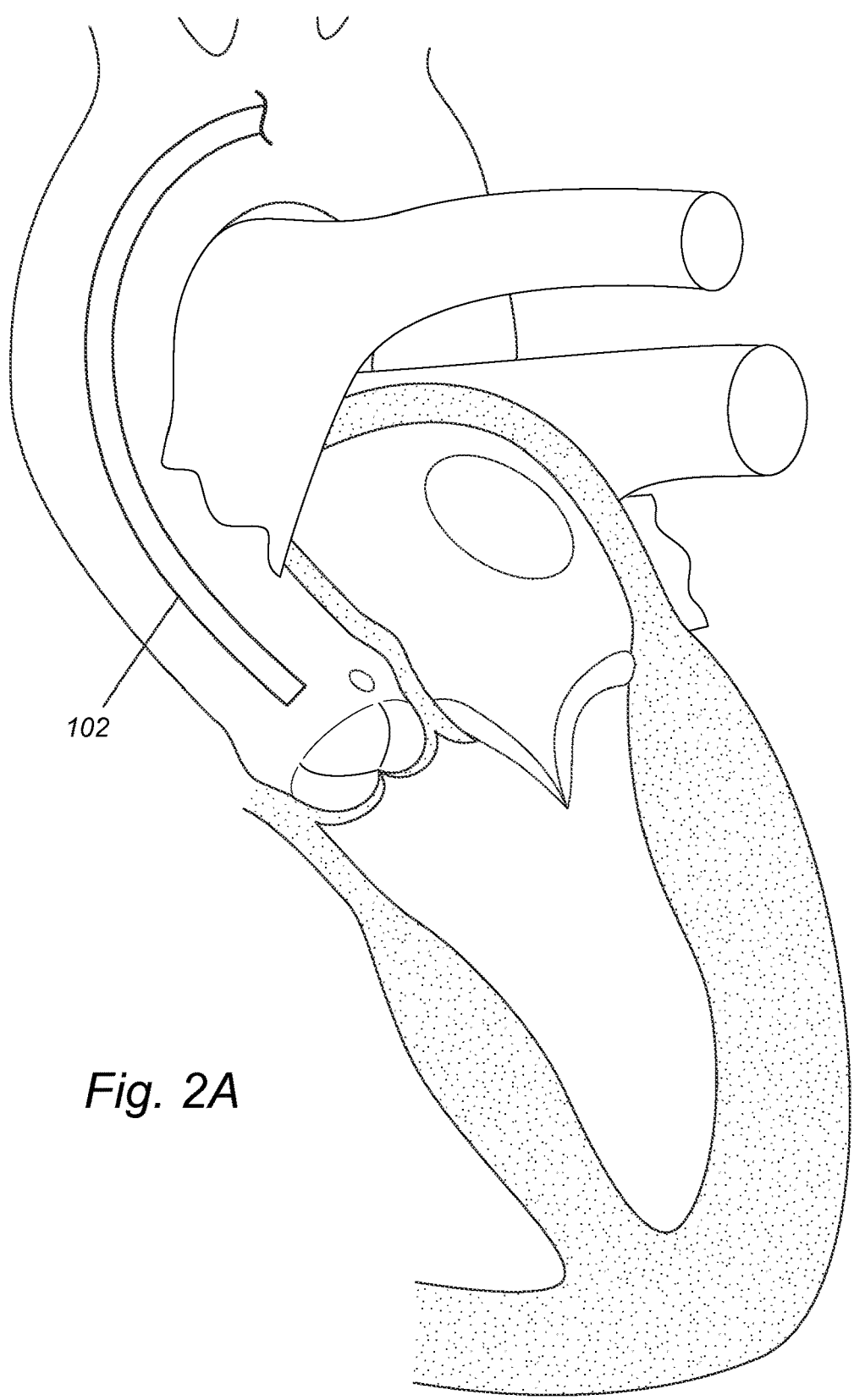
FIGS. 2A-E depict, in accordance with various embodiments of the present invention, a method of using an exemplar device of the invention for imaging an aortic valve complex.
Figure 2B:
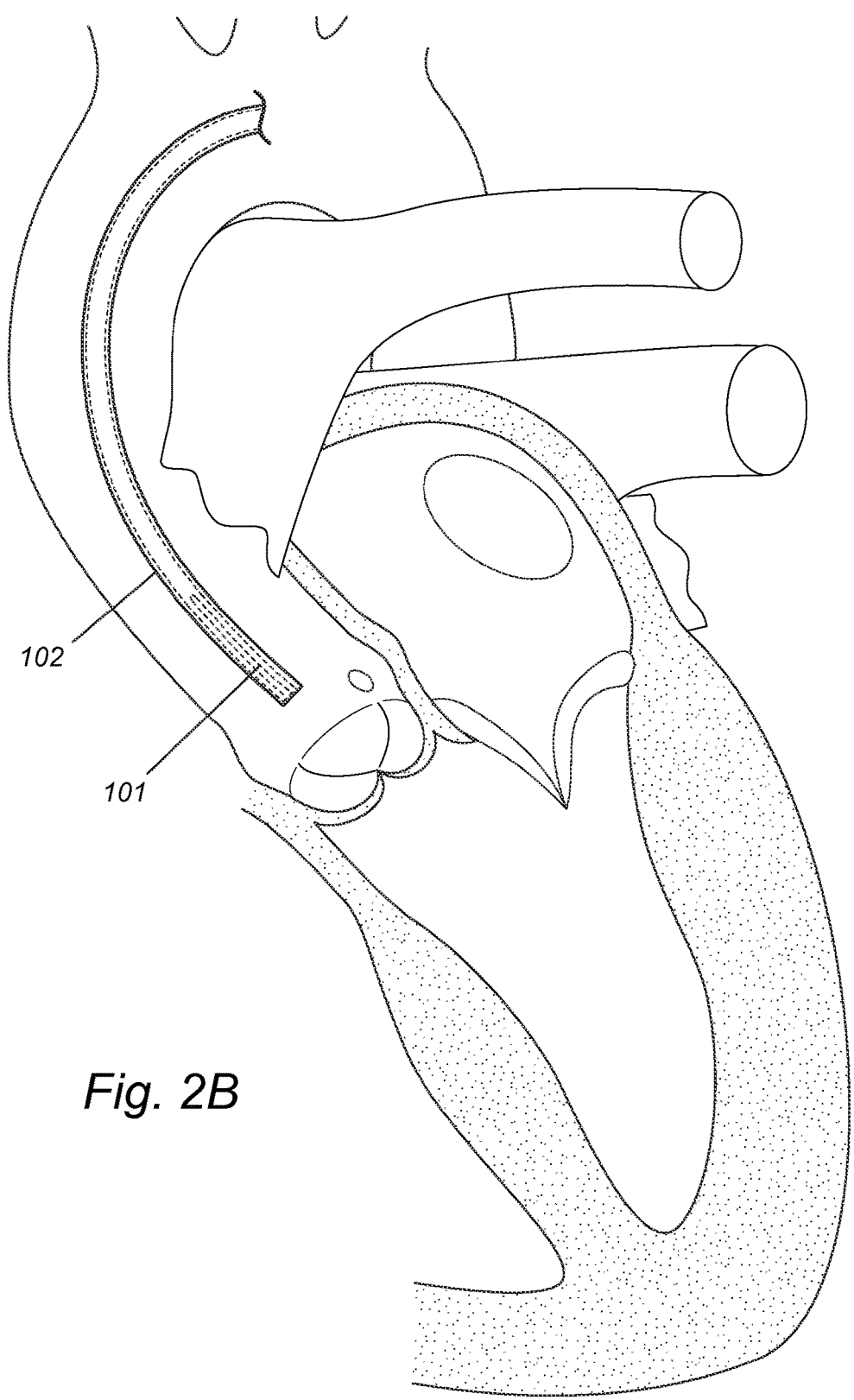

A non-limiting example of a method according to the present disclosure is shown in FIGS. 2A-E. In some embodiments, standard steps may be performed, including induction of anesthesia (local or general), sterile preparation and other necessary and standard steps in a transcatheter and percutaneous operation (for example, incising and/or preclosing an artery, threading and/or removing a guidewire, and inserting and/or withdrawing a catheter). FIG. 2A illustrates an outer sheath 102 that has been maneuvered to reach the sinotubular junction of a subject via transfemoral, transaxillary/subclavian, or transaortic route. Some routine steps are not shown or described here. For example, a guidewire may be mounted to the outer sheath's distal end to guide the outer sheath through the subject's vasculature system. Then, a catheter 101 may be inserted into the outer sheath 102. As the outer sheath 102 encloses the distal portion of the catheter 101, the three distal branches 105 are flattened and become relatively straight inside the outer sheath 102. FIG. 2B illustrates the catheter 101 advanced to the distal end of the outer sheath 102. (FIG. 2B). Then, catheter 101 may be further advanced, so that the distal end of the catheter 101 may extend from the outer sheath 102 exposing the distal branches 105 so they are no longer restrained by the sheath 102.

Figure 2C:
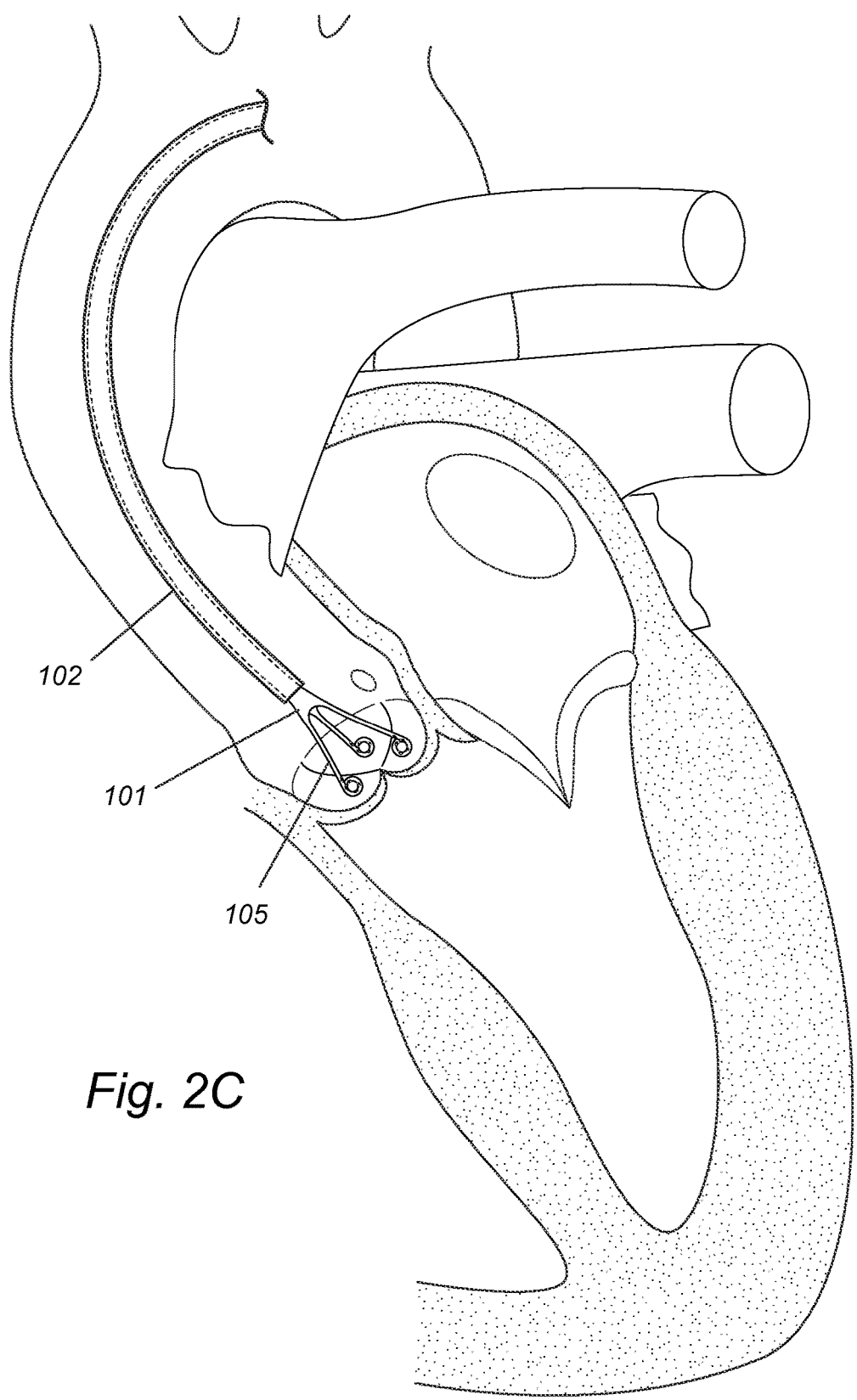
Figure 2D:
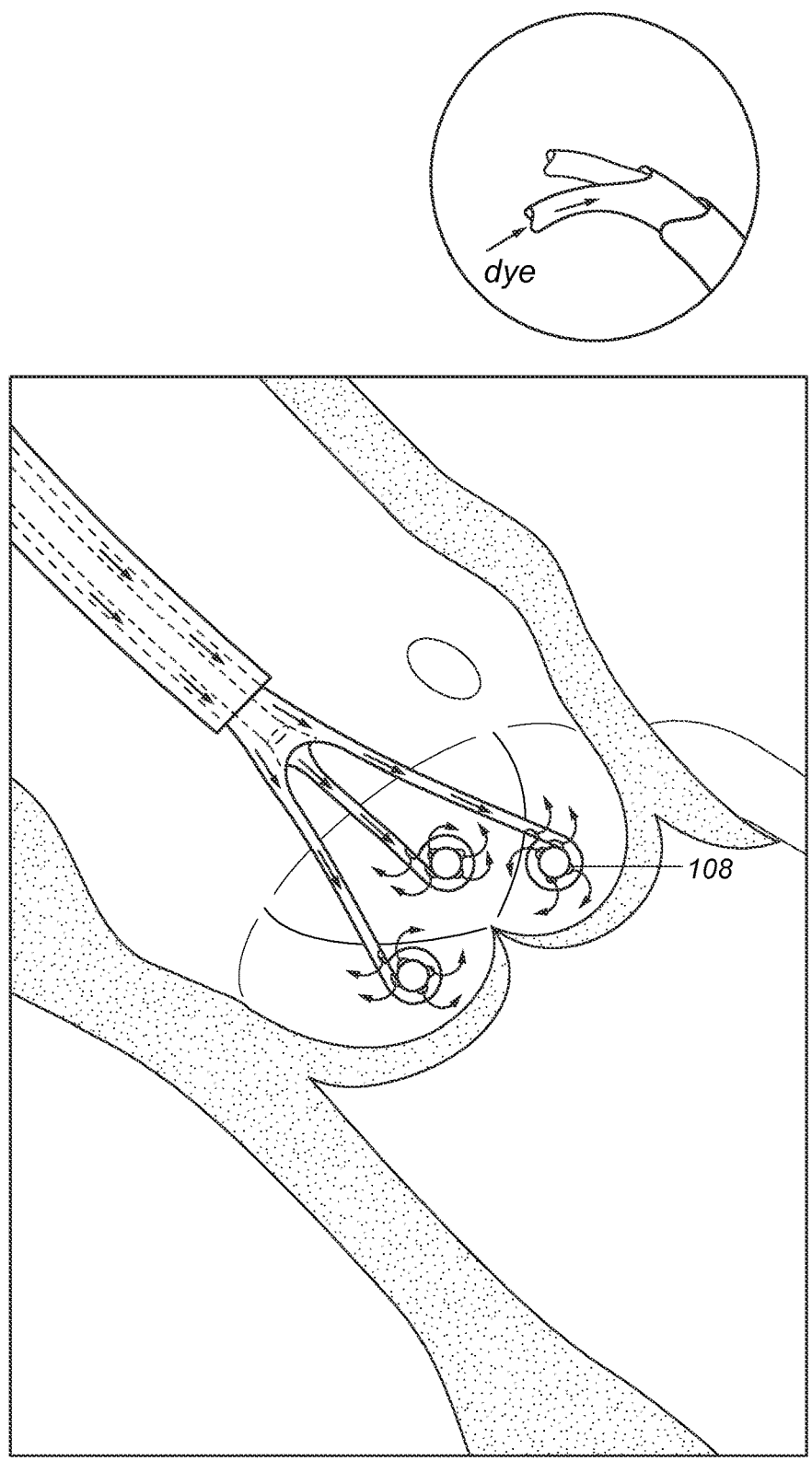

In some three branch 105 embodiments, the three distal branches 105 may then assume their natural orientation by fanning out with the tips evenly spaced apart from each other. In some embodiments, the tips may also curl into a pigtail or J form. Then, the three pigtail branches 105 may be navigated to engage the three aortic leaflets in the aortic valve complex (FIG. 2C). FIG. 2C illustrates the tips of the branches 105 navigated to be in close proximity to the leaflets of the aortic valve. In some embodiments, the tips may be touching the leaflets of the aortic valve. In other embodiments, the tips may only get close to the leaflets. In other embodiments, the cross-sectional diameter of the tips or pigtails may be equal or slightly larger than the aortic space near the aortic valve. This will allow the tips to naturally orient the catheter into position and center the lumen in the valve. The tips can then be brought to just touching the valve or base of the valve leaflets, and also touching the sidewalls of the aortic valve and space. In other embodiments, the tips of the distal branches 105 may naturally fall into depressions or wells formed by the flat portion and/or base of each leaflet as illustrated in FIG. 2C. This will allow a physician to appropriately navigate the catheter 101 into position using tactile feedback from the aortic valve. In this non-limiting example, at or near the distal end of each of the three digital branches 105, there are one or more side openings 108. In some embodiments, a contrast dye may then be injected into the peripheral lumen inlet 104, through the peripheral lumen, out of the side openings 108 on the three distal branches 105, and directly to each of the three aortic leaflets (FIG. 2D). Then, once the dye has been injected, the aortic valve complex may be imaged using standard imaging technologies and with the aid of the contrast dye.

In some of the three branch embodiments, where each of the three distal branches 105 engages (e.g. closely abuts, touches or comes within close proximity) one of the three aortic leaflets, a contrast dye can be directly injected into each aortic leaflet to minimize the injection frequency and amount. Also, since the three distal branches 105 may be configured to be equally spaced from one another on a radial plane and aligned with the three aortic leaflets, a clear visualization of a co-axial radiographic projection of the aortic valve complex can be achieved to guide a user to best orientate and implant a TAVR device (e.g., a replacement heart valve). In accordance with the present invention, a TAVR procedure may be performed before, during, or after imaging the aortic valve complex.

Figure 2E:
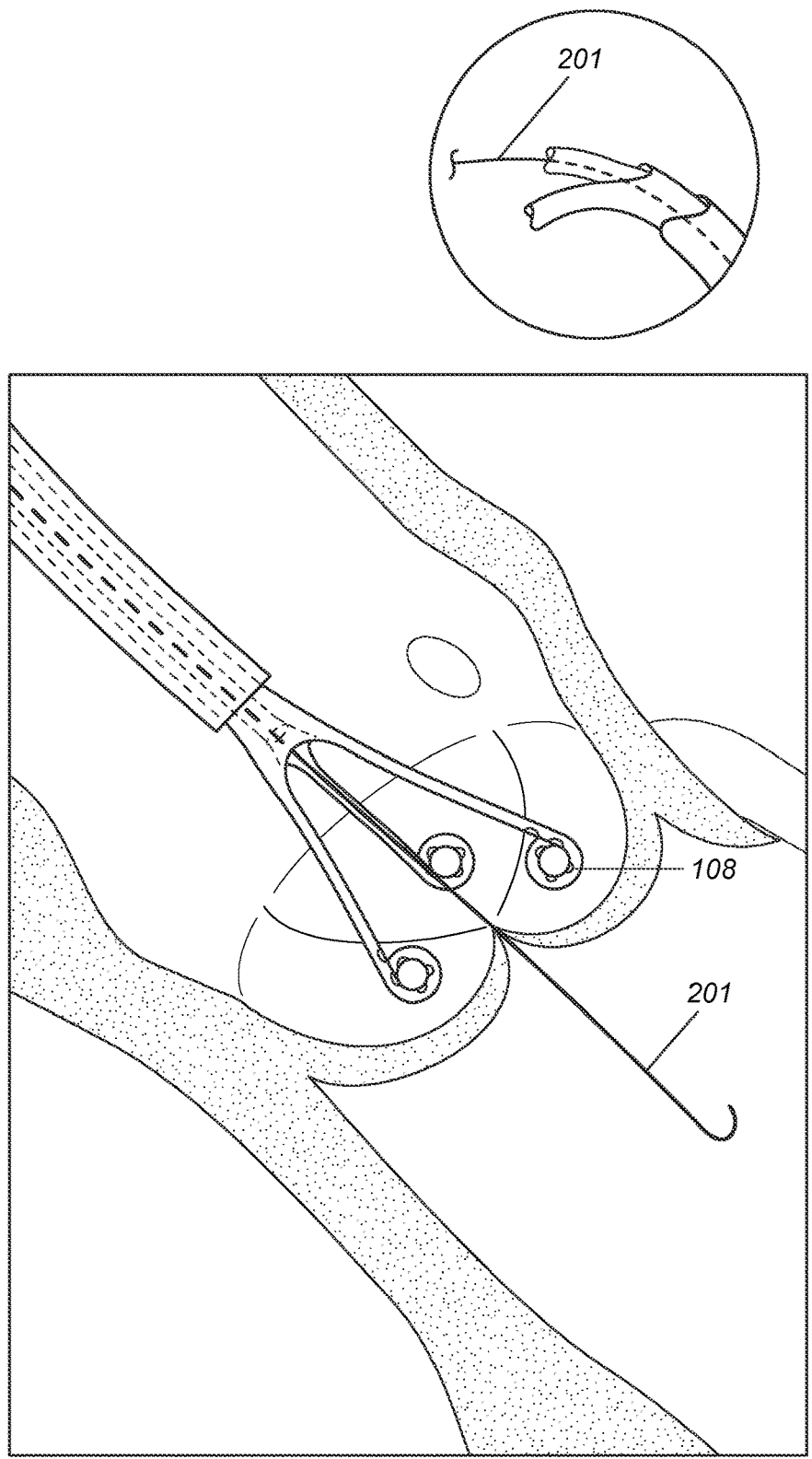

In addition, after the alignment of the catheter 101 tips with the aortic valve leaflets, the distal end of the catheter is then centered with respect to a cross sectional plane of the aortic valve complex. Accordingly, the central lumen of the catheter 101 is also co-axially aligned with the aortic valve orifice, and thus another instrument 201 (e.g., a guidewire, a catheter, and/or a pressure sensor) can be passed through the central lumen through the aortic valve orifice, in order to cross the aortic valve retrogradely in a more efficient manner. Accordingly, and as illustrated in FIG. 2E, an instrument 201 (for example, a guidewire) may be inserted into the central lumen inlet 103, through the central lumen, out of the distal opening of the central lumen, further across the aortic valve orifice and into the left ventricle.

Other standard steps within the procedure include heparinization and that the artery incision is closed either by manual compression, suture-mediated pre-closure or surgical closure. The procedure may be performed by local anesthesia with conscious sedation or general anesthesia, in which case the patient is generally woken up immediately after the procedure. Heparinization may be reversed at the end of the procedure by administration of protamine. Heparin intolerant individuals may be anticoagulated during the procedure using direct thrombin inhibitors.

Example 3

Figure 3A:
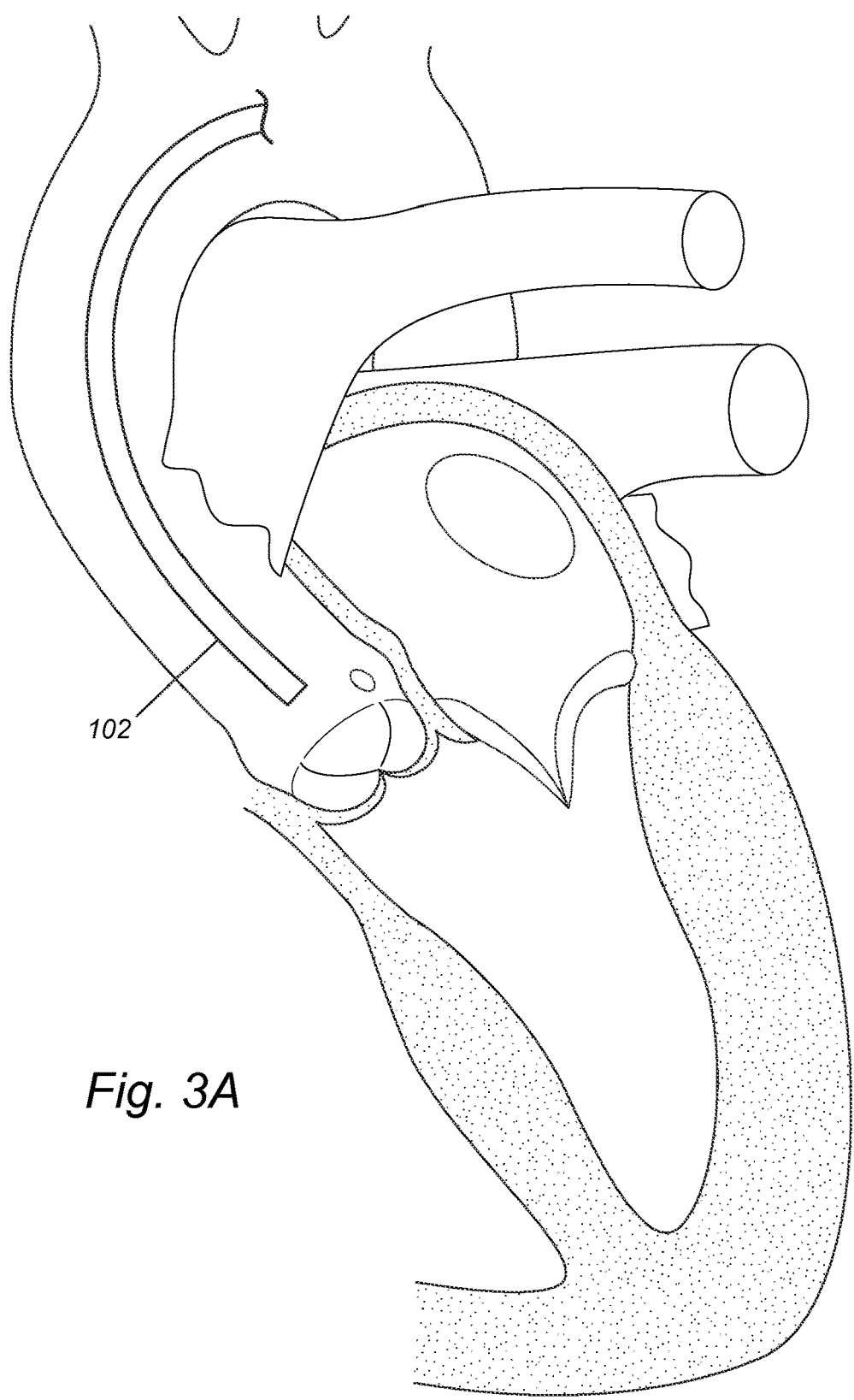
FIGS. 3A-D depict, in accordance with various embodiments of the present invention, a method of using an exemplar device of the invention for imaging an aortic valve complex.
Figure 3B:
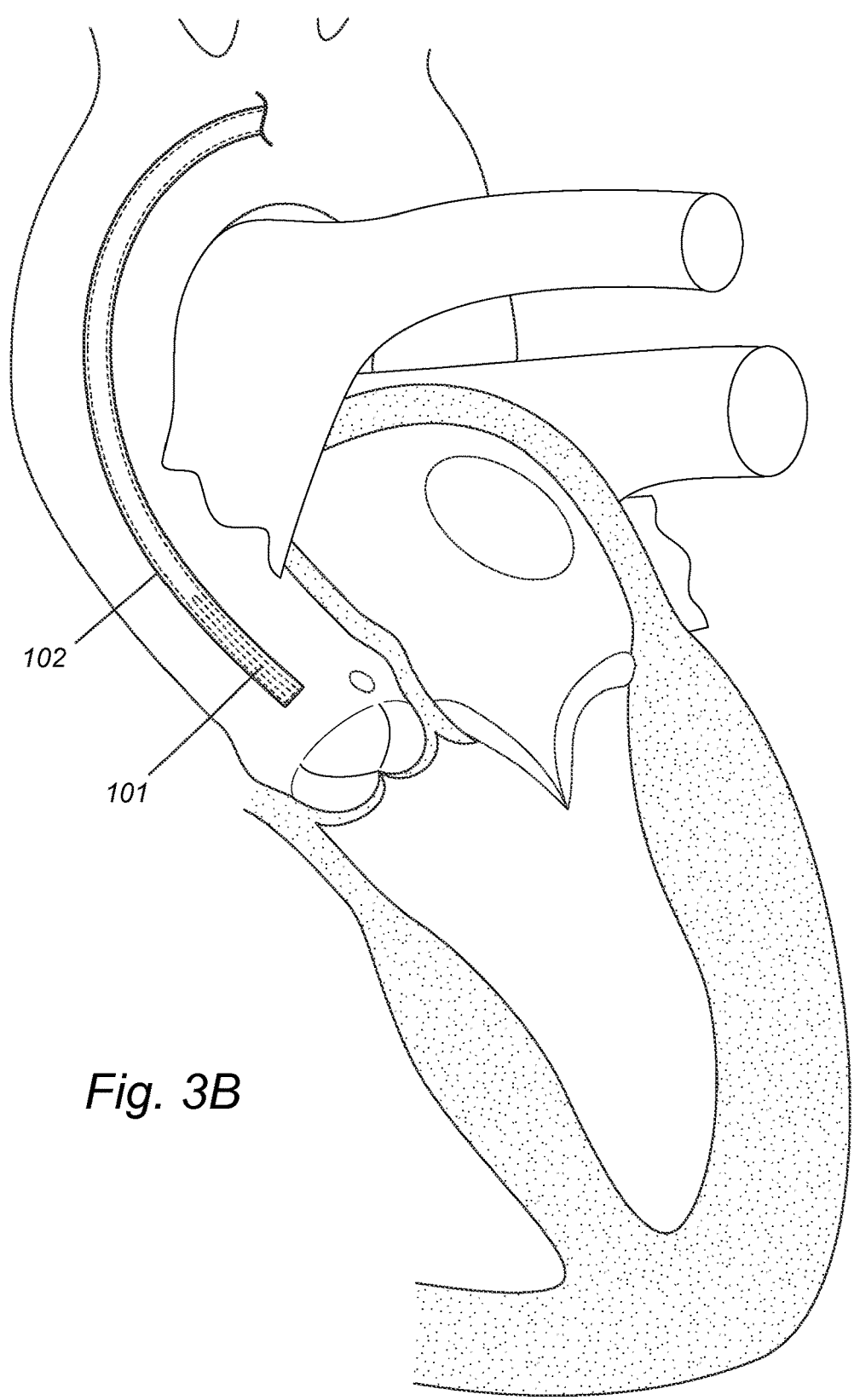
Figure 3C:
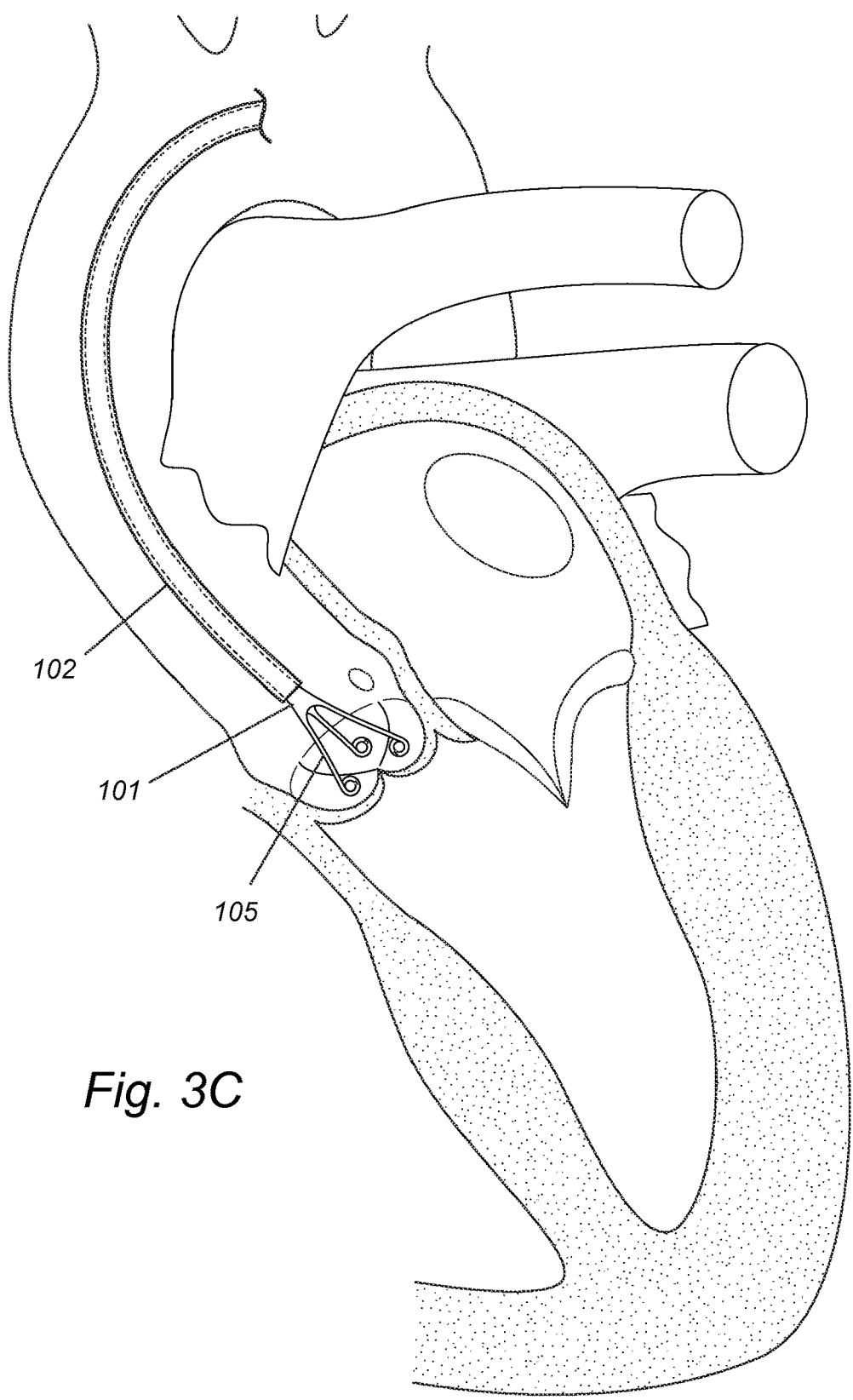

Another non-limiting example of the method is shown in FIGS. 3A-E. After induction of anesthesia, a caregiver may perform sterile preparation and other necessary and standard steps in a transcatheter and percutaneous operation (for example, incising and/or pre-closing an artery, threading and/or removing a guidewire, and inserting and/or withdrawing a catheter). As illustrated in FIG. 3A, an outer sheath 102 may be maneuvered to reach the sinotubular junction of a subject via transfemoral, transaxillary/subclavian, or transaortic route. Some routine steps are not shown or described here. For example, a guidewire may be mounted to the outer sheath's distal end to guide the outer sheath through the subject's vasculature system. A catheter 101 may then be inserted into the outer sheath 102 and advanced to the distal end of the outer sheath 102. As illustrated in FIG. 3B, while the outer sheath 102 encloses the distal portion of the catheter 101, the three distal branches 105 (in this embodiment) are relatively straighten inside the outer sheath 102. Then, once the distal end of the catheter 101 is advanced out of the outer sheath 102 allowing the distal branches 105 to fan out into a position so each tip is equally spaced from each of the other two tips. In some embodiments, the three distal branches 105 curl into a pigtail or J form. Then, as illustrated in FIG. 3C, the catheter 101 and pigtails may be navigated to engage (e.g., touch, come within close proximity, or slide into a depression formed by each leaflet) the three aortic leaflets in the aortic valve complex. In this non-limiting example, at or near the distal end of each of the three digital branches 105, there is a radiographic marker (e.g., a radiopaque or radiodense marker). After the tips are in position with respect to the leaflets, the aortic valve complex may be imaged with the aid of the radiographic markers. In addition, a contrast dye may be used for imaging the aortic valve complex. For instance, the three distal branches 105 may also have side openings 109 at or near their distal ends (FIG. 4C), and a contrast dye is injected into the peripheral lumen inlet 104, through the peripheral lumen, out of the side openings 109 on the three distal branches 105, and directly to each of the three aortic leaflets to aid imaging.

Since, in this embodiment, the three distal branches are equally spaced from one another on a radial plane and aligned with the three aortic leaflets, a clear visualization of a co-axial radiographic projection of the aortic valve complex can be achieved to guide a user to best orientate and implant a TAVR device (e.g., a replacement heart valve). In accordance with the present invention, a TAVR procedure may be performed before, during, or after imaging the aortic valve complex. In other embodiments, there may be other numbers of distal branches. For example, there may be six distal branches, where pairs of distal branches are equally spaced for one another.

Figure 3D:
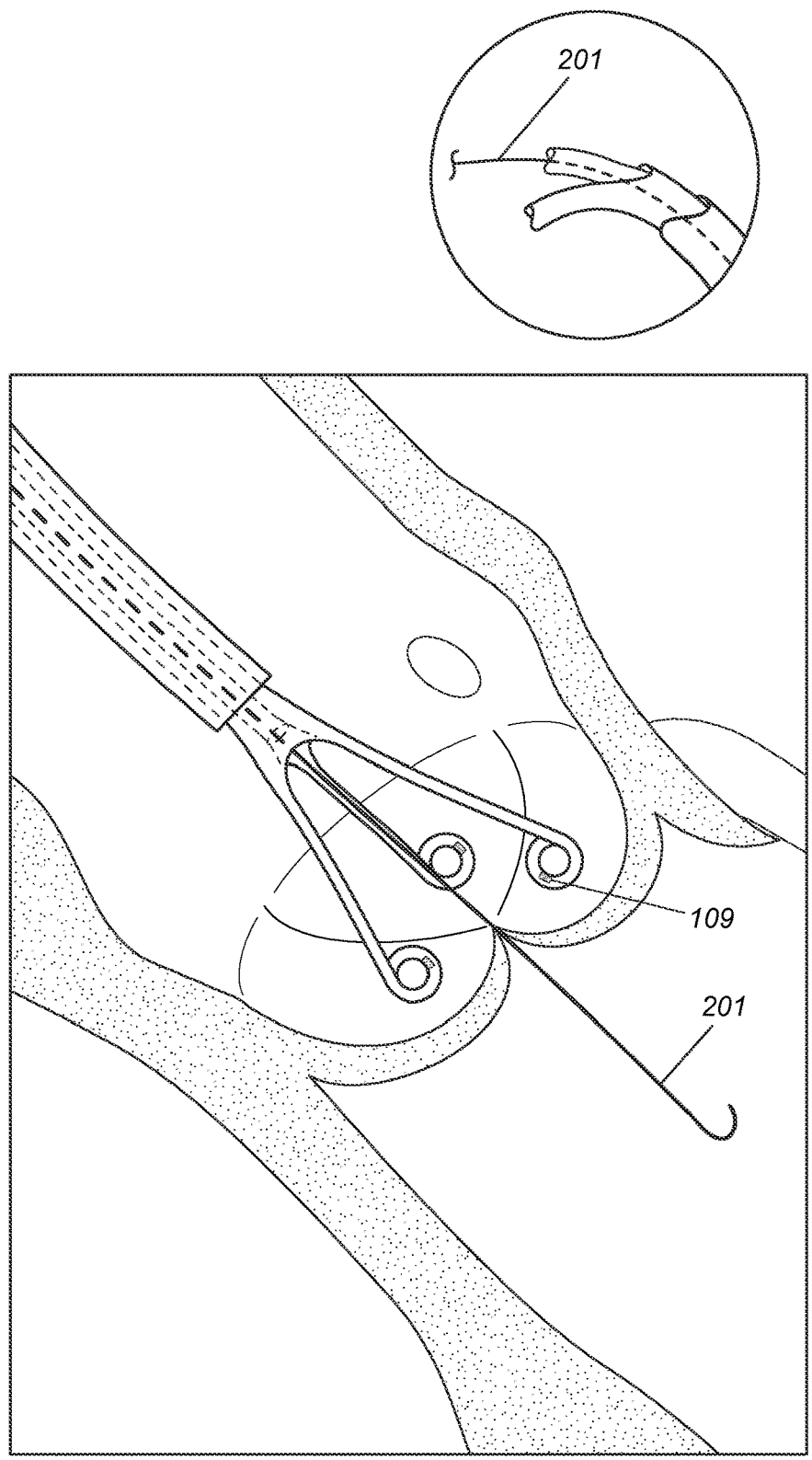

In addition, because in this three branch 105 embodiment, the central lumen is also co-axially aligned with the aortic valve orifice, another instrument 201 (e.g., a guidewire, a catheter, and/or a pressure sensor) can be passed through the central lumen to cross the aortic valve retrogradely in a more efficient manner. In accordance with the present invention, an instrument 201 (for example, a guidewire) may be inserted into the central lumen inlet 103, through the central lumen, out of the distal opening of the central lumen, further across the aortic valve orifice and into the left ventricle (FIG. 3D).

Other standard steps within the procedure include heparinization and that the artery incision is closed either by manual compression, suture-mediated pre-closure or surgical closure. The procedure may be performed by local anesthesia with conscious sedation or general anesthesia, in which case the patient is generally woken up immediately after the procedure. Heparinization may be reversed at the end of the procedure by administration of protamine. Heparin intolerant individuals may be anticoagulated during the procedure using direct thrombin inhibitors.

Figure 4A:
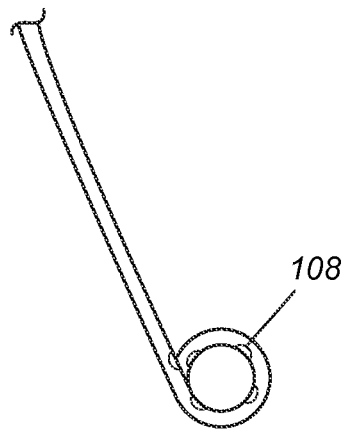
FIGS. 4A-C depict, in accordance with various embodiments of the present invention, three non-limiting examples of the distal branch with side openings 108 and/or radiographic markers 109.
Figure 4B:
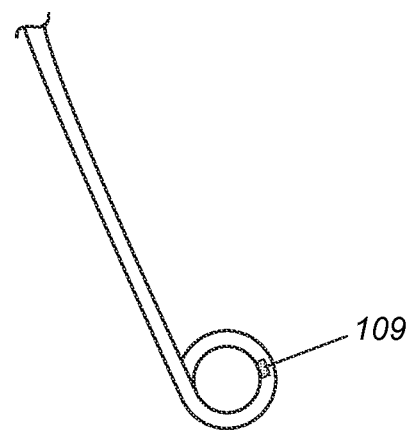
Figure 4C:
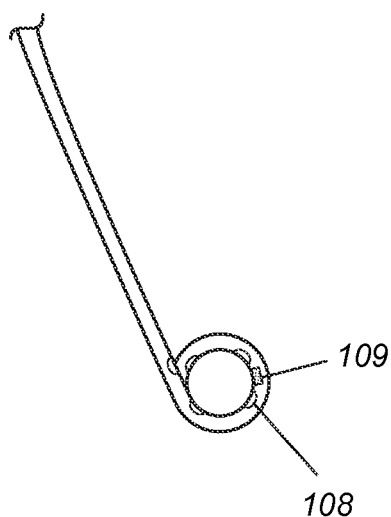

FIGS. 4A-4C illustrate different embodiments of the distal branches 105 of a catheter 101 as disclosed herein. FIG. 4A discloses a distal branch 105 that includes side openings 108 that are equally spaced around a loop of distal branch 105. FIG. 4B illustrates a distal branch 105 that includes a radiographic marker 109. FIG. 4C illustrates a distal branch 105 that includes a radiographic marker 109 and side openings 108. As disclosed herein, the side openings 108 and radiographic markers 109 may be various sizes, shapes and orientations, and may be distributed in different patterns and spatial orientations along the distal branches 105. Accordingly, FIGS. 4A-4C only provide examples of potential configurations.

Figure 5:
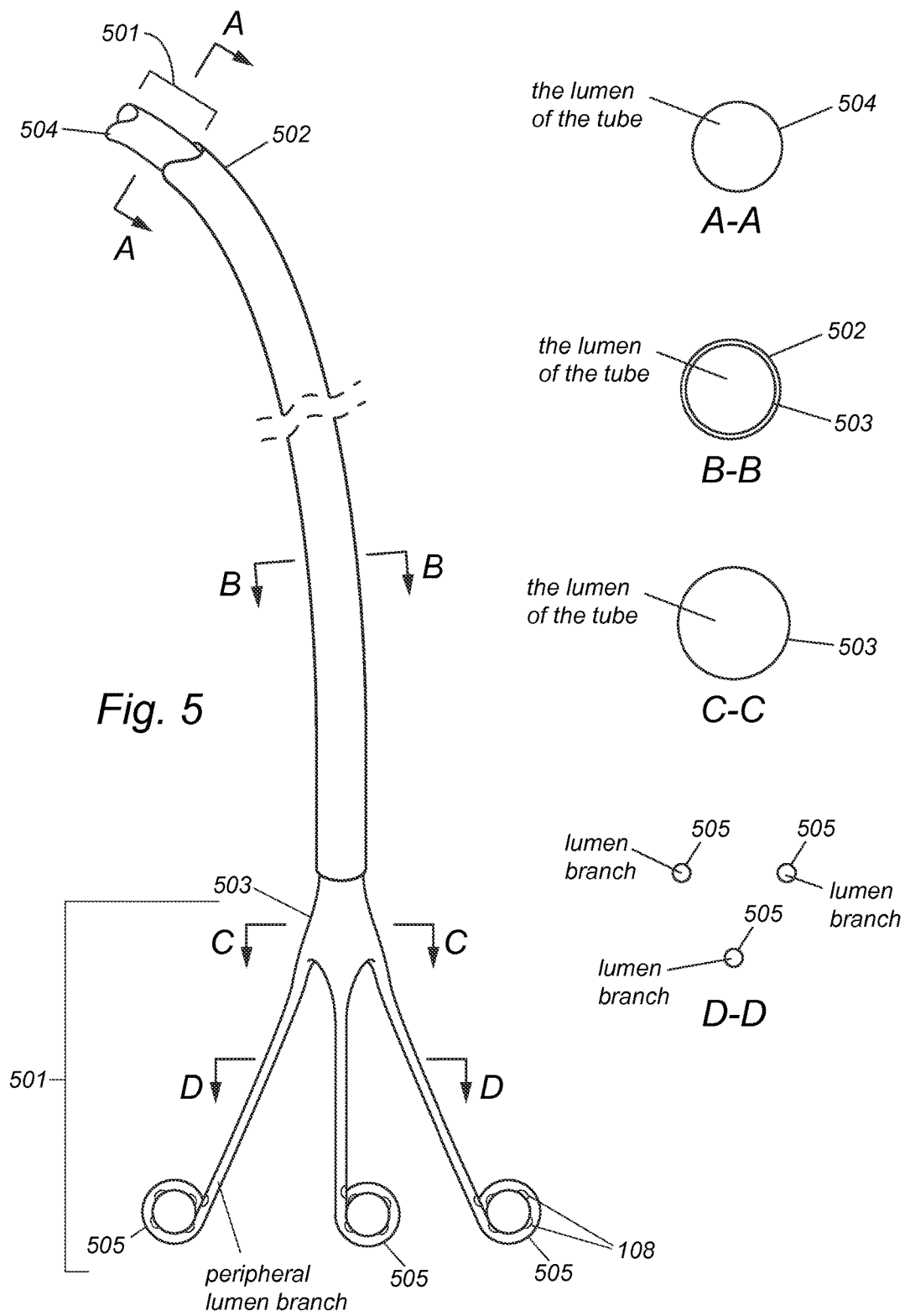
FIG. 5 depicts, depicts a longitudinal cross sectional view of an embodiment of a catheter (501), an outer sheath covering the catheter (502), a wall of the catheter (503), an inlet (504), and three distal branches of the catheter (505). Panel A-A is a cross-section view of the device at its proximal end. Panel B-B is a cross-section view of the proximal portion of the device. Panel C-C is a cross-section view of the center portion of the device. Panel D-D is a cross-section view of the distal portion of the device. Panel E-E is a cross-section view of the three distal branches 505 on the distal portion of the device. Along the longitudinal axis of the catheter (501), the wall (503) forms one tube at the center portion and forms three distal branches (505) at the distal portion. Accordingly, the lumen of the tube branches into three lumen branches inside the two, three, four or more distal branches. At or near its distal end, the distal branch can comprise one or more side openings, one radiographic marker, or both (see FIGS. 4A-C).

FIG. 5 depicts a longitudinal cross sectional view of an embodiment of a catheter (501), an outer sheath covering the catheter (502), a wall of the catheter (503), an inlet (504), and three distal branches of the catheter (505). Panel A-A is a cross-section view of the device at its proximal end. Panel B-B is a cross-section view of the proximal portion of the device. Panel C-C is a cross-section view of the center portion of the device. Panel D-D is a cross-section view of the distal portion of the device. Panel E-E is a cross-section view of the three distal branches 505 on the distal portion of the device. Along the longitudinal axis of the catheter (501), the wall (503) forms one tube at the center portion and forms three distal branches (505) at the distal portion. Accordingly, the lumen of the tube branches into three lumen branches inside the two, three, four or more distal branches. At or near its distal end, the distal branch can comprise one or more side openings, one radiographic marker, or both (see FIGS. 4A-C). In this embodiment, the catheter 501 does not include an interior wall or separate lumens. Rather, one single lumen is utilized, for example, to inject contrast dye that may exist the side openings 108. This catheter accordingly may have a simplified construction relative to embodiments with multiple lumens.

Additional Embodiments of Devices and Systems

Various additional embodiments of the present invention provide for a device for imaging an aortic valve complex and/or for advancing an instrument across an aortic valve retrogradely. The device may include: a catheter comprising an interior wall and an exterior wall, wherein the catheter has a proximal portion, a distal portion, and a center portion between the proximal portion and the distal portion. The interior wall forms a central lumen along the longitudinal axis of the catheter. The interior wall and the exterior wall form a peripheral lumen around the central lumen along the longitudinal axis of the catheter. The interior wall and the exterior wall form two, three, four or more distal branches at the distal portion of the catheter, and the peripheral lumen branches into two, three, four or more peripheral lumen branches inside the two, three, four or more distal branches.

In various embodiments, each of the two, three, four or more distal branches comprises one or more side openings at or near the distal end of the distal branch. In various embodiments, each of the two, three, four or more distal branches comprises one radiographic marker at or near the distal end of the distal branch.

In some embodiments, the radiographic markers or identifiers comprise a material having a radiopacity different from (greater or less than) the radiopacity of the distal branches, such as radiopaque and/or radiodense materials (for non-limiting examples, gold, tantalum and platinum). In some embodiments, the radiographic markers can be separate from the distal branches and coupled thereto. In other embodiments, the radiographic markers can be integrally formed within the distal branches and can be distinguished from the remainder of the distal branches by radiodense characteristics. Still in accordance with the invention, the two, three, four or more distal branches can be made of or impregnated with a radiopaque or radiodense material so that they are detected by and visualized on the imaging equipment. If the branches are made of or impregnated with radiopaque or radiodense material, the distal branches serve as radiographic markers themselves. For example, the three radiographic markers denote a triangle disposed on a plane that is perpendicular and co-axial to the longitudinal axis of the device.

While it is described that the two, three, four or more distal branches are formed by the interior wall and the exterior wall at the catheter's distal portion, one of ordinary skill the art would understand that the interior wall and the exterior wall are not necessarily two separate components with a defined boundary. Because their surfaces are continuous from each other from a topological point of view, the interior wall and the exterior wall may be two relative areas without a defined boundary on one integral component. For example, in some embodiments, it is contemplated that a raw material may be molded into a catheter, in which the two walls are made simultaneously and together as one piece. Of course, the interior wall and the exterior wall may be two separate components with a defined boundary. For example, in other embodiments, it is contemplated that the two walls are made separately first and then connected with a defined boundary to produce a catheter. However, still in accordance with the present invention, the two walls may be made separately first and then fused to produce a catheter, in which a defined boundary between the two walls is eliminated after fusion.

In various embodiments, the length of the catheter may be but is not limited to any one or more of about 90-300 cm, 50-90 cm, 100-150 cm, 150-200 cm, 200-250 cm, 250-300 cm or 300-350 cm.

In various embodiments, the diameter of the catheter may be but is not limited to any one or more of about 4-23 Fr, 4-10 Fr, 10-15 Fr, 15-20 Fr, 20-25 Fr, 25-30 Fr or 30-35 Fr.

In various embodiments, the length of the outer sheath may be but is not limited to any one or more of about 80-290 cm, 50-100 cm, 100-150 cm, 150-200 cm, 200-250 cm, or 250-300 cm.

In various embodiments, the diameter of the outer sheath may be but is not limited to any one or more of about 5-24 Fr, 4-10 Fr, 10-15 Fr, 15-20 Fr, 20-25 Fr, 25-30 Fr or 30-35 Fr.

In various embodiments, the diameter of the tubular interior wall may be but is not limited to any one or more of about 1-6 Fr, 1-2 Fr, 2-3 Fr, 3-4 Fr, 4-5 Fr, 5-6 Fr, 1-3 Fr, 4-6 Fr, 6-8 Fr or 8-10 Fr.

In various embodiments, the diameter of the tubular exterior wall may be but is not limited to any one or more of about 2-8 Fr, 1-6 Fr, 1-2 Fr, 2-3 Fr, 3-4 Fr, 4-5 Fr, 5-6 Fr, 1-3 Fr, 4-6 Fr, 6-8 Fr or 8-10 Fr.

In various embodiments, the length of the two, three, four or more distal branches may be but is not limited to any one or more of about 2-20 cm, 2-5 cm, 5-10 cm, 10-15 cm, 15-20 cm, 5-15 cm or 10-20 cm.

In various embodiments, the diameter of the two, three, four or more distal branches may be but is not limited to any one or more of about 1-6 Fr, 1-2 Fr, 2-3 Fr, 3-4 Fr, 4-5 Fr, 5-6 Fr, 1-3 Fr, 4-6 Fr, 6-8 Fr or 8-10 Fr.

In various embodiments, the interior wall forms a first inlet of the central lumen at the proximal portion of the catheter. In various embodiments, the exterior wall forms a second inlet of the peripheral lumen at the proximal portion of the catheter.

In various embodiments, the two, three, four or more distal branches are pigtail-shaped or J-shaped. In various embodiments, the two, three, four or more distal branches are equally spaced from one another on a radial plane perpendicular to the longitudinal axis of the catheter.

In various embodiments, the device further comprises an outer sheath enclosing the catheter, wherein the two, three, four or more distal branches are straightened when the outer sheath encloses the distal portion of the catheter, and wherein the two, three, four or more distal branches are pigtail-shaped or J-shaped when the outer sheath does not enclose the distal portion of the catheter. In certain embodiments, the outer sheath further comprises a shaft, hook, ring, loop, or nose on its distal end for mounting a guidewire.

In various embodiments, the device further comprises a contrast dye, wherein the contrast dye is injected into the peripheral lumen. Examples of the contrast dye include but are not limited to Iodine-based contrast media such as iohexol, iodixanol and ioversol.

In various embodiments, the device further comprises an instrument, wherein the instrument is inserted into the central lumen. Examples of the instrument include but are not limited to a delivery system for BAV or TAVR, tube, sheath, guidewire, catheter, balloon, stent, needle, and pressure sensor. In various embodiments, the device further comprises a tube, wherein the tube is inserted into the central lumen and can be advanced or refracted independently. For example, the tube may be advanced over a guidewire to cross a valve or stenosis independent from the other components of the device. In one embodiment, the central lumen of the catheter is relatively large (8-24 Fr) and acts as a long sheath for a balloon aortic valvuloplasty (BAV) balloon or TAVR delivery system. In a further embodiment, the device comprises a mechanism (e.g., a radiographic maker) for aligning the ridges, lines, points or alternative markers of the central lumen and the BAV or TAVR delivery system to facilitate precise rotational positioning of the BAV or TAVR delivery system in relation to the three native aortic valve leaflets.

In various embodiments, each of the two, three, four or more distal branches engages one heart valve leaflet. In various embodiments, the central lumen is co-axially aligned with a heart valve orifice.

Various embodiments of the present invention provide for a device for imaging an aortic valve complex. The device may include a catheter comprising a wall, wherein the catheter has a proximal portion, a distal portion, and a center portion between the proximal portion and the distal portion. The wall forms one tube along the longitudinal axis of the catheter at the center portion and forms two, three, four or more distal branches at the distal portion. Accordingly, the lumen of the tube branches into two, three, four or more lumen branches inside the two, three, four or more distal branches. In various embodiments, each of the two, three, four or more distal branches comprises one or more side openings at or near the distal end of the distal branch. In various embodiments, each of the two, three, four or more distal branches comprises one radiographic marker at or near the distal end of the distal branch. In various embodiments, the wall forms an inlet of the tube at the proximal portion of the catheter. In various embodiments, the two, three, four or more distal branches are pigtail-shaped or J-shaped. In various embodiments, the two, three, four or more distal branches are equally spaced from one another on a radial plane perpendicular to the longitudinal axis of the catheter. In various embodiments, the device further comprises an outer sheath enclosing the catheter, wherein the two, three, four or more distal branches are straightened when the outer sheath encloses the distal portion of the catheter, and wherein the two, three, four or more distal branches are pigtail-shaped or J-shaped when the outer sheath does not enclose the distal portion of the catheter. In various embodiments, the device further comprises a contrast dye, wherein the contrast dye is injected into the tube. In various embodiments, each of the two, three, four or more distal branches engages one heart valve leaflet.

In accordance with the invention, the number of distal branches corresponds to the number of leaflets in a native valve to be imaged and/or treated. For example, when the valve of interest is the mitral valve, which has two leaflets, a device having two distal branches would be employed. Still as another example, when a subject has an anatomical variation that the native aortic valve is bicuspid rather than tricuspid, a device having two rather than three distal branches is employed in correspondence to the two-leaflet structure of the native aortic valve.

Methods

Various embodiments of the present invention provide for a method for imaging an aortic valve complex. The method may include the following steps: (1) providing an outer sheath; (2) maneuvering the outer sheath to reach the sinotubular junction or aortic root, just above the aortic valve, of a subject; (3) providing a device comprising: a catheter comprising an interior wall and an exterior wall, wherein the catheter has a proximal portion, a distal portion, and a center portion between the proximal portion and the distal portion, wherein the interior wall forms a central lumen along the longitudinal axis of the catheter, wherein the interior wall and the exterior wall form a peripheral lumen around the central lumen along the longitudinal axis of the catheter, wherein the interior wall and the exterior wall form two, three, four or more distal branches at the distal portion of the catheter, wherein the peripheral lumen branches into two, three, four or more peripheral lumen branches inside the two, three, four or more distal branches, and wherein each of the two, three, four or more distal branches comprises one or more side openings at or near the distal end of the distal branch; (4) inserting the device into the outer sheath, wherein the two, three, four or more distal branches are straightened inside the outer sheath; (5) advancing the device out of the outer sheath, wherein the two, three, four or more distal branches are pigtail-shaped or J-shaped outside the outer sheath; (6) engaging each aortic leaflet of the subject with one distal branch; (7) injecting a contrast dye to the aortic valve complex of the subject through the peripheral lumen; and (8) imaging the aortic valve complex of the subject.

Various embodiments of the present invention provide for a method for imaging an aortic valve complex. The method may include the following steps: (1) providing an outer sheath; (2) maneuvering the outer sheath to reach the sinotubular junction of a subject or aortic root, just above the aortic valve; (3) providing a device comprising: a catheter comprising an interior wall and an exterior wall, wherein the catheter has a proximal portion, a distal portion, and a center portion between the proximal portion and the distal portion, wherein the interior wall forms a central lumen along the longitudinal axis of the catheter, wherein the interior wall and the exterior wall form a peripheral lumen around the central lumen along the longitudinal axis of the catheter, wherein the interior wall and the exterior wall form two, three, four or more distal branches at the distal portion of the catheter, wherein the peripheral lumen branches into two, three, four or more peripheral lumen branches inside the two, three, four or more distal branches, and wherein each of the two, three, four or more distal branches comprises one radiographic marker at or near the distal end of the distal branch; (4) inserting the device into the outer sheath, wherein the two, three, four or more distal branches are straightened inside the outer sheath; (5) advancing the device out of the outer sheath, wherein the two, three, four or more distal branches are pigtail-shaped or J-shaped outside the outer sheath; (6) engaging each aortic leaflet of the subject with one distal branch; and (7) imaging the aortic valve complex of the subject and the radiographic markers.

Various embodiments of the present invention provide for a method for imaging an aortic valve complex. The method may include the following steps: (1) providing an outer sheath; (2) maneuvering the outer sheath to reach the sinotubular junction of a subject or aortic root, just above the aortic valve; (3) providing a device comprising: a catheter comprising an interior wall and an exterior wall, wherein the catheter has a proximal portion, a distal portion, and a center portion between the proximal portion and the distal portion, wherein the interior wall forms a central lumen along the longitudinal axis of the catheter, wherein the interior wall and the exterior wall form a peripheral lumen around the central lumen along the longitudinal axis of the catheter, wherein the interior wall and the exterior wall form two, three, four or more distal branches at the distal portion of the catheter, wherein the peripheral lumen branches into two, three, four or more peripheral lumen branches inside the two, three, four or more distal branches, and wherein each of the two, three, four or more distal branches comprises one radiographic marker and one or more side openings at or near the distal end of the distal branch; (4) inserting the device into the outer sheath, wherein the two, three, four or more distal branches are straightened inside the outer sheath; (5) advancing the device out of the outer sheath, wherein the two, three, four or more distal branches are pigtail-shaped or J-shaped outside the outer sheath; (6) engaging each aortic leaflet of the subject with one distal branch; and (7) imaging the aortic valve complex of the subject and the radiographic markers. In various embodiments, the method further comprises, prior to step (7), injecting a contrast dye to the aortic valve complex of the subject through the peripheral lumen.

Various embodiments of the present invention provide for a method for imaging an aortic valve complex. The method may include the following steps: (1) providing an outer sheath; (2) maneuvering the outer sheath to reach the sinotubular junction or aortic root, just above the aortic valve, of a subject; (3) providing a device, comprising: a catheter comprising a wall, wherein the catheter has a proximal portion, a distal portion, and a center portion between the proximal portion and the distal portion, wherein the wall forms one tube along the longitudinal axis of the catheter at the center portion and forms two, three, four or more distal branches at the distal portion, wherein the lumen of the tube branches into two, three, four or more lumen branches inside the two, three, four or more distal branches; (4) inserting the device into the outer sheath, wherein the two, three, four or more distal branches are straightened inside the outer sheath; (5) advancing the device out of the outer sheath, wherein the two, three, four or more distal branches are pigtail-shaped or J-shaped outside the outer sheath; (6) engaging each aortic leaflet of the subject with one distal branch; (7) injecting a contrast dye to the aortic valve complex of the subject through the catheter; and (8) imaging the aortic valve complex of the subject.

While the steps of the methods are described sequentially, one of ordinary skill the art would understand that the sequence of steps may be shuffled or altered. For example, the device can be inserted into the outer sheath first and then the device and the outer sheath can be maneuvered as a whole through the subject's vasculature system to reach the sinotubular junction.

In various embodiments, transfemoral, transaxillary/subclavian or transaortic access routes are used for maneuvering the outer sheath to reach the sinotubular junction of the subject.

In various embodiments, the aortic valve complex is imaged with X-ray, fluoroscopy, CT, ultrasound (intravascular or echocardiography) or MRI. In various embodiments, the image device detects the dye evacuated from the side openings and/or detects the radiographic marker impregnated in the distal arms.

In various embodiments, the method further comprises inserting an instrument into the central lumen and advancing the instrument through the aortic valve orifice into the left ventricle. Examples of the instrument include but are not limited to tube, sheath, guidewire, catheter, balloon, stent, needle, and pressure sensor. Still in accordance with the present invention, the methods further comprises inserting a BAV or TAVR delivery device into the central lumen and delivering a BAV or TAVR device to the aortic valve.

In various embodiments, the method further comprises performing a BAV or TAVR procedure. In accordance with the present invention, the BAV or TAVR procedure may be performed before, during, or after imaging the aortic valve complex.

Also in accordance with the present invention, as TAVR is a known surgical procedure, one of ordinary skill in the art would readily recognize that the method could involve other additional steps, which are not described in details here. These additional steps include, but are not limited to, anesthesia, sterilization, heparinization, accessing the patient's heart via various routes such as femoral, transseptal, transaortic and transapical approaches, ventricular pacing, stitching of the access site or percutaneous femoral closure. For example, more information on these procedures are described in Ye et al. (Transapical aortic valve implantation in humans. Ye J, Cheung A, Lichtenstein S V, Carere R G, Thompson C R, Pasupati S, Webb J G. J Thorac Cardiovasc Surg. 2006 May; 131(5):1194-6), Lichtenstein et al. (Transapical transcatheter aortic valve implantation in humans: initial clinical experience. Lichtenstein S V, Cheung A, Ye J, Thompson C R, Carere R G, Pasupati S, Webb J G. Circulation. 2006 Aug. 8; 114 (6):591-6. Epub 2006 Jul. 31), Kurra et al. (Pre-procedural imaging of aortic root orientation and dimensions: comparison between X-ray angiographic planar imaging and 3-dimensional multidetector row computed tomography. Kurra V, Kapadia S R, Tuzcu E M, Halliburton S S, Svensson L, Roselli E E, Schoenhagen P. JACC Cardiovasc Interv. 2010 January; 3 (1):105-13.), Wake et al. (Computed tomography angiography for transcatheter aortic valve replacement. Wake N, Kumamaru K, Prior R, Rybicki F J, Steigner M L. Radiol Technol. 2013 March-April; 84(4):326-40.), and Little et al. (Multimodality noninvasive imaging for transcatheter aortic valve implantation: a primer. Little S H, Shah D J, Mahmarian J J. Methodist Debakey Cardiovasc J. 2012 April-June; 8(2): 29-37.), all of which are incorporated by reference herein in their entirety as fully set forth.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, Dictionary of Microbiology and Molecular Biology $3^{rd}$ ed., revised ed., J. Wiley & Sons (New York, N.Y. 2006); Smith, March's Advanced Organic Chemistry Reactions, Mechanisms and Structure $7^{th}$ ed., J. Wiley & Sons (New York, N.Y. 2013); Singleton, Dictionary of DNA and Genome Technology $3^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2$^{nd}$ ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 July, 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Definitions

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. In various embodiments, the pathologic condition is aortic stenosis or aortic regurgitation, mitral stenosis or mitral regurgitation, tricuspid stenosis or tricuspid regurgitation, pulmonic stenosis or pulmonic regurgitation, any vessel stenosis that requires a balloon or stent therapy, any aneurysmal vessel that requires a stent therapy, any vascular sac that requires a vascular closure, including but not limited to the left atrial appendage. In accordance with the invention, the number of distal branches is configured to correspond to the number of leaflets in a native valve of interest. For instance, when the valve of interest is the mitral valve, which has two leaflets, a device having correspondingly two distal branches would be employed.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. In various embodiments, the disease condition is aortic stenosis or aortic regurgitation, mitral stenosis or mitral regurgitation, tricuspid stenosis or tricuspid regurgitation, pulmonic stenosis or pulmonic regurgitation, any vessel stenosis that requires a balloon or stent therapy, any aneurysmal vessel that requires a stent therapy, any vascular sac that requires a vascular closure, including but not limited to the left atrial appendage. In accordance with the invention, the number of distal branches is configured to correspond to the number of leaflets in a native valve of interest. For instance, when the valve of interest is the mitral valve, which has two leaflets, a device having correspondingly two distal branches would be employed.

In various embodiments, the devices, systems and methods described herein are configured for humans. One of skill in the art would readily appreciate that the devices, systems and methods described herein could be customized for use in almost any mammal in which a heart valve may be replaced.

"Mammal" as used herein refers to any member of the class Mammalia, including but not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult and newborn subjects, as well as fetuses, whether male or female, are intended to be included within the scope of this term.

In various embodiments, a replacement heart valve is a prosthetic valve or a bioprosthetic valve. In accordance with the present invention, a prosthetic valve is made of purely artificial or non-biological materials, and a bioprosthetic valve is made of animal tissues alone or in combination with artificial or non-biological materials. Materials which may be used to construct a replacement heart valve are well known in the art, for example as described in U.S. Publication No. US2011/0319989, which is incorporated by reference herein in its entirety as fully set forth.

In various embodiments, a replacement heart valve is self-expandable or balloon expandable. Examples of self-expandable valves include, but are not limited to, MEDTRONIC COREVALVE, which is constructed with a nitinol self-expanding valve stent frame and porcine pericardial leaflets. Examples of balloon-expandable valves include, but are not limited to, EDWARDS SAPIEN XT VALVE, which is constructed with a cobalt-chromium balloon-expandable valve stent frame and bovine pericardial leaflets.

In various embodiments, the appropriate guide wires, sheaths and catheters for use with the devices, systems and methods described herein will be apparent to a person of skill in the art, for example, as described in Ye et al. (Transapical aortic valve implantation in humans. Ye J, Cheung A, Lichtenstein S V, Carere R G, Thompson C R, Pasupati S, Webb J G. J Thorac Cardiovasc Surg. 2006 May; 131(5):1194-6), Lichtenstein et al. (Transapical transcatheter aortic valve implantation in humans: initial clinical experience. Lichtenstein S V, Cheung A, Ye J, Thompson C R, Carere R G, Pasupati S, Webb J G. Circulation. 2006 Aug. 8; 114 (6):591-6. Epub 2006 Jul. 31), Kurra et al. (Pre-procedural imaging of aortic root orientation and dimensions: comparison between X-ray angiographic planar imaging and 3-dimensional multidetector row computed tomography. Kurra V, Kapadia S R, Tuzcu E M, Halliburton S S, Svensson L, Roselli E E, Schoenhagen P. JACC Cardiovasc Interv. 2010 January; 3 (1):105-13.), Wake et al. (Computed tomography angiography for transcatheter aortic valve replacement. Wake N, Kumamaru K, Prior R, Rybicki F J, Steigner M L. Radiol Technol. 2013 March-April; 84(4):326-40.), and Little et al. (Multimodality noninvasive imaging for transcatheter aortic valve implantation: a primer. Little S H, Shah D J, Mahmarian J J. Methodist Debakey Cardiovasc J. 2012 April-June; 8(2):29-37.), all of which are incorporated by reference herein in their entirety as fully set forth.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A device, comprising:
    a catheter comprising an interior wall and an exterior wall,
        wherein the catheter has a proximal portion, a distal portion, and a center portion between the proximal portion and the distal portion,
        wherein the interior wall forms a central lumen along the longitudinal axis of the catheter,
        wherein the interior wall and the exterior wall form a single peripheral lumen around the central lumen along the longitudinal axis of the catheter,
        wherein the interior wall and the exterior wall form at least three distal branches at a fixed branch point of the distal portion of the catheter, wherein the central lumen terminates in a fixed opening at the fixed branch point, and the at least three distal branches fan out and retain an orientation at the fixed branch point, spaced from each other, when unrestrained;
        wherein the single peripheral lumen branches into at least three peripheral lumen branches inside the at least three distal branches, wherein the at least three peripheral lumen branches are all in fluid communication with each other and the single peripheral lumen; and
        wherein each of the at least three distal branches comprises one or more side openings at or near the distal end.

2. The device of claim 1, wherein each of the at least three distal branches comprises one radiographic marker at or near the distal end of the distal branch.

3. The device of claim 1, wherein the interior wall forms a first inlet of the central lumen at the proximal portion of the catheter.

4. The device of claim 1, wherein the exterior wall forms a second inlet of the peripheral lumen at the proximal portion of the catheter.

5. The device of claim 1, wherein the at least three distal branches are pigtail-shaped or J-shaped and may be advanced independently of each other.

6. The device of claim 1, wherein the at least three distal branches are curved.

7. The device of claim 1, wherein the at least three distal branches have rounded tips.

8. The device of claim 1, wherein the at least three distal branches are configured to be equally spaced from one another on a radial plane perpendicular to the longitudinal axis of the catheter when not physically restrained by a sheath.

9. The device of claim 1, further comprising an outer sheath enclosing the catheter, wherein the at least three distal branches are straightened when the outer sheath encloses the distal portion of the catheter, and wherein the at least distal branches are pigtail-shaped or J-shaped when the outer sheath does not enclose the distal portion of the catheter.

10. The device of claim 1, further comprising a contrast dye or drug, wherein the contrast dye or drug is injected into the single peripheral lumen.

11. The device of claim 1, further comprising an instrument, wherein the instrument is inserted into the central lumen.

12. The device of claim 1, further comprising a tube, wherein the tube is inserted into the central lumen and can be advanced or retracted independently.

13. The device of claim 1, wherein the central lumen is co-axially aligned with a heart valve orifice.

14. A method, comprising:
providing an outer sheath;
maneuvering the outer sheath to reach the sinotubular junction or aortic root just above the aortic valve of a subject;
providing the device of claim 1;
inserting the device into the outer sheath;
advancing the device out of the outer sheath, wherein the at least three distal branches are J-shaped outside the outer sheath;
maneuvering the catheter into a position that brings each aortic leaflet of the subject within proximity to one distal branch;
injecting a contrast dye to the aortic valve complex of the subject through the peripheral lumen of the device; and
imaging the aortic valve complex of the subject.

15. The method of claim 14, wherein the aortic valve complex is imaged with X-ray, fluoroscopy, ultrasound, computerized tomography (CT), or magnetic resonance imaging (MRI).

16. The method of claim 14, wherein proximity comprises physical contact.

17. The method of claim 14, further comprising inserting an instrument into the central lumen and advancing the instrument through the aortic valve orifice into the left ventricle.

18. The method of claim 14, further comprising performing a balloon aortic valvuloplasty (BAV) or transcatheter aortic valve replacement (TAVR) procedure.

19. A method, comprising:
providing an outer sheath;
maneuvering the outer sheath to reach the sinotubular junction or aortic root just above the aortic valve of a subject;
providing the device of claim 3;
inserting the device into the outer sheath, wherein the at least three branches are straightened inside the outer sheath;
advancing the device out of the outer sheath, wherein the at least three distal branches are J-shaped outside the outer sheath;
maneuvering the device in order to position each aortic leaflet of the subject within proximity to one distal branch; and
imaging the aortic valve complex of the subject and the radiographic markers.

20. The method of claim 19, wherein the aortic valve complex is imaged with X-ray, fluoroscopy, ultrasound, CT or MRI.

21. The method of claim 19, further comprising inserting an instrument into the central lumen and advancing the instrument through the aortic valve orifice into the left ventricle.

22. The method of claim 19, further comprising performing a BAV or TAVR procedure.

* * * * *